US009481660B2

(12) United States Patent
Heller et al.

(10) Patent No.: US 9,481,660 B2
(45) Date of Patent: Nov. 1, 2016

(54) TETRA-O-SUBSTITUTED BUTANE-BRIDGE MODIFIED NDGA DERIVATIVES, THEIR SYNTHESIS AND PHARMACEUTICAL USE

(71) Applicants: Jonathan Daniel Heller, San Francisco, FL (US); Qingqi Chen, Chapel Hill, NC (US); Rocio Alejandra Lopez, Raleigh, NC (US); Amanda Jean Morris, Graham, NC (US)

(72) Inventors: Jonathan Daniel Heller, San Francisco, FL (US); Qingqi Chen, Chapel Hill, NC (US); Rocio Alejandra Lopez, Raleigh, NC (US); Amanda Jean Morris, Graham, NC (US)

(73) Assignee: ERimos Pharmaceuticals, LLC, Houston, TX (US)

( * ) Notice: Subject to any disclaimer, the term of this patent is extended or adjusted under 35 U.S.C. 154(b) by 0 days.

(21) Appl. No.: 14/246,741

(22) Filed: Apr. 7, 2014

(65) Prior Publication Data
US 2014/0221384 A1    Aug. 7, 2014

Related U.S. Application Data

(60) Continuation of application No. 13/561,517, filed on Jul. 30, 2012, now Pat. No. 8,691,845, which is a division of application No. 12/443,926, filed as application No. PCT/US2007/080231 on Oct. 2, 2007, now Pat. No. 8,232,277.

(60) Provisional application No. 60/827,783, filed on Oct. 2, 2006.

(51) Int. Cl.
| | |
|---|---|
| C07C 33/26 | (2006.01) |
| C07D 295/088 | (2006.01) |
| C07C 37/50 | (2006.01) |
| C07C 39/367 | (2006.01) |
| C07C 43/225 | (2006.01) |
| C07C 43/23 | (2006.01) |
| C07C 47/27 | (2006.01) |
| C07C 47/273 | (2006.01) |
| C07C 217/20 | (2006.01) |
| C07D 277/24 | (2006.01) |
| C07C 39/21 | (2006.01) |
| C07C 43/205 | (2006.01) |
| C07C 217/54 | (2006.01) |

(52) U.S. Cl.
CPC ........... *C07D 295/088* (2013.01); *C07C 37/50* (2013.01); *C07C 39/21* (2013.01); *C07C 39/367* (2013.01); *C07C 43/2055* (2013.01); *C07C 43/225* (2013.01); *C07C 43/23* (2013.01); *C07C 47/27* (2013.01); *C07C 47/273* (2013.01); *C07C 217/20* (2013.01); *C07C 217/54* (2013.01); *C07D 277/24* (2013.01)

(58) Field of Classification Search
CPC ...................................................... C07C 33/26
See application file for complete search history.

(56) References Cited

U.S. PATENT DOCUMENTS

| | | |
|---|---|---|
| 6,579,880 B2 | 6/2003 | Weidner-Wells et al. |
| 7,741,357 B1 | 6/2010 | Huang et al. |

FOREIGN PATENT DOCUMENTS

| | | |
|---|---|---|
| WO | 8803805 | 6/1988 |
| WO | WO8803805 * | 6/1988 |
| WO | 2006081363 | 8/2006 |

OTHER PUBLICATIONS

Berge, Pharmaceutical Salts, Jan. 1997, Journal of Pharmaceutical Sciences, vol. 66, No. 1, p. 1-19.
"Clinical Trials", http://www.erimos.com/clinical_trials, accessed Jul. 19, 2011.
Plaza, Inhibitory Effect of Nordihydroguaiaretic Acid and its Tetra-acetylated Derivative, 2008, In Vivo, vol. 22, p. 353-362.
Prophylactic Definition, http://www.medterms.com/script/main/art.asp?articlekey-11902, accessed Jul. 18, 2011.
Xia, et al., An Efficient Synthetic Method of Nordihydroguaiaretic, 2003, Chinese Chemical Letters, vol. 14, p. 359-360.
Lu, et al., 2010, Med. Sci. Monit, vol. 16, No. 5, p. 1-15.
Mak, et al., Leukemia & Lymphoma, vol. 48, No. 4, p. 774-785.

* cited by examiner

*Primary Examiner* — Michael Barker
*Assistant Examiner* — Karen Cheng
(74) *Attorney, Agent, or Firm* — Keller Life Science Law, PA

(57) ABSTRACT

The present invention relates to nordihydroguaiaretic acid derivative compounds, namely, butane bridge modified nordihydroguaiaretic acid (NDGA) compounds and butane bridge modified tetra-O-substituted NDGA compounds, pharmaceutical compositions containing them, methods of making them, and methods of using them and kits including them for the treatment of diseases and disorders, in particular, diseases resulting from or associated with a virus infection, such as HIV infection, HPV infection, or HSV infection, an inflammatory disease, such as various types of arthritis and inflammatory bowel diseases, metabolic diseases, such as diabetes and hypertension, or a proliferative disease, such as diverse types of cancers.

12 Claims, No Drawings

TETRA-O-SUBSTITUTED BUTANE-BRIDGE MODIFIED NDGA DERIVATIVES, THEIR SYNTHESIS AND PHARMACEUTICAL USE

CROSS-REFERENCE TO RELATED APPLICATIONS

This application is a continuation of application 13/561,517, filed on Jul. 30, 2012, now U.S. Pat. No. 8,691,845, which is a divisional application of U.S. patent application Ser. No. 12/443,926, filed May 18, 2009, which is an U.S. National Phase application under 35 U.S.C. §371 of International Patent Application No. PCT/US2007/080231, filed Oct. 2, 2007, which claims the benefit of U.S. Provisional Application No. 60/827,783, filed Oct. 2, 2006; the contents of which are incorporated herein by reference in their entirety.

BACKGROUND OF THE INVENTION

The present invention relates to nordihydroguaiaretic acid derivatives, methods of making them and methods of using them for treating viral infections, inflammatory diseases, metabolic diseases, vascular (including cardiovascular) diseases and proliferative diseases, such as cancer.

Nordihydroguaiaretic acid (NDGA, Formula I) has the following chemical structure, in which there are two catechol groups, and a 2,3-dimethylbutane bridge. The butane bridge links two catechol moieties through a 4 position. NDGA is a natural compound that can be isolated from the resin of the leaves of *Larrea tridentate*, a desert plant indigenous to the southwestern United States and Mexico. It has a meso-form conformation of (2S,3R), which is the symmetric structure, and is not optical active.

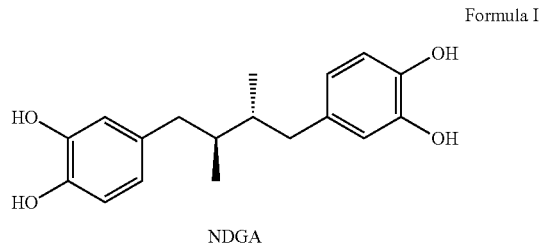 [SMILES: C[C@H](Cc1ccc(O)c(O)c1)[C@@H](C)Cc1ccc(O)c(O)c1]

Formula I

NDGA

Research on NDGA and its derivatives has been attracting increasing interest recently. A large number of NDGA derivatives have been reported, and could be classified as the following:

Type 1: ether bonded NDGA, the most common NDGA derivatives, in which a substituted group is chemically bonded to one or more of the hydroxy groups of the catechol moieties.

Type 2: ester bonded NDGA derivatives, in which a substituted group is covalently bonded to one or more of the hydroxy groups of the catechol moieties.

Type 3: end-ring NDGA derivatives, in which two hydroxy groups at the catechol moieties were linked together to form 5-6 member rings through ether or carbonate bonds.

Type 4: di-substituted NDGA derivatives, in which one hydroxy group of the catechol is methylated, the other one is covalently bonded to a substituted group.

Type 5: phenyl ring modifications, in which the substituted groups are chemically linked to the phenyl ring.

Type 6: Butane bridge modifications, in which two methyl groups in the bridge were removed or modified by substituted groups.

NDGA and its synthetic derivatives have numerous characteristics. Being a lipoxygenases inhibitor, NDGA can induce cystic nephropathy in the rat.[1] In addition, it shows various bioactivities, including inhibition of protein kinase C,[2] induction of apoptosis,[3] alterations of the cellular membrane,[4] elevation of cellular $Ca^{2+}$ level[5] and activation of $Ca^{2+}$ channels in smooth muscle cells,[6] breakdown of preformed Alzheimer's beta-amyloid fibrils in vitro,[7] anti-oxidation,[8] etc. This natural product NDGA is used commercially as a food additive to preserve fats and butter in some parts of the world. Recently, the derivatives of the plant lignan NDGA have been used to block viral replication through the inhibition of viral transcription.[9-16] These compounds can inhibit production of human immunodeficiency virus (HIV),[9-13] herpes simlex virus (HSV),[14,15] and human papillomavirus (HPV) transcripts[16] by deactivation of their Sp1-dependent promoters. Moreover, (tetra-O-methyl)nordihydroguaiaretic acid ($M_4N$, Formula II, terameprocol) can function as an anti-HIV proviral transcription inhibitor and causes growth arrest of a variety of transformed human and mouse cells in culture and in mice.[17-19] Compound $M_4N$ is currently in clinical trials against human cancers.

While $M_4N$ (Formula II) is a strikingly effective and non-toxic anticancer agent, $M_4N$ and several other methylated NDGAs, all show poor water solubility which somewhat limit their application for certain drug action studies. To circumvent this problem, a water soluble derivative of NDGA, (tetra-O-dimethylglycyl)nordihydroguaiaretic acid ($G_4N$, Formula III) has been designed and synthesized.[11,18]

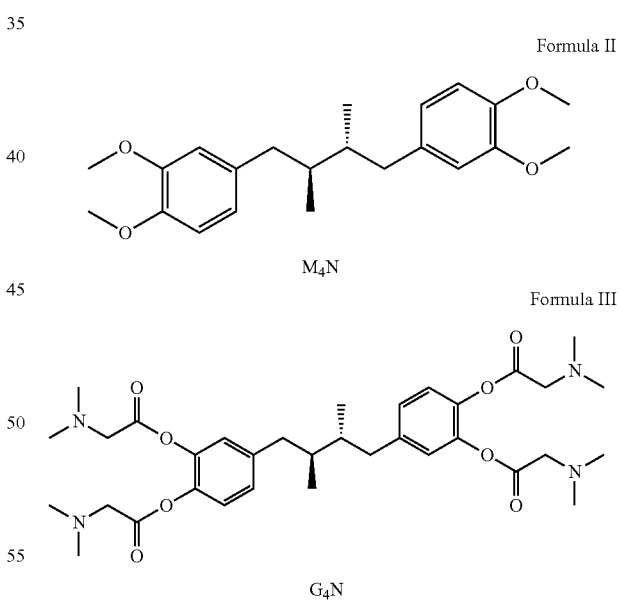

Formula II $M_4N$

Formula III $G_4N$ $G_4N$ is a very effective mutation-insensitive inhibitor to HIV-1, HSV-1 and HSV-2.[17,22] However, it is somewhat unstable and has a relatively short half-life in aqueous solution, reportedly due to the ester bonds connecting the dimethyl glycine moieties on the NDGA main skeleton.[18]

Therefore, there is a need for NDGA derivatives, some with improved water solubility, as well as good stability, both as water soluble compound and as hydrophobic compounds having the desired pharmaceutical effects. The inventors have developed new derivatives of NDGA that have these advantages and will be useful in therapeutic compositions and treatment methods.

BRIEF SUMMARY OF THE INVENTION

The present invention relates to nordihydroguaiaretic acid derivative compounds, pharmaceutical compositions, methods of making them, and methods of using them and kits including them for the treatment of diseases and disorders, in particular, diseases resulting from or associated with a virus infection, an inflammatory disease, a metabolic disease, a vascular disease or a proliferative disease.

The present invention is based on research stemming from the inventors' realization that 1,4-bis(catechol-4-yl)-butane (Formula IV), a double-demethylated NDGA, showed 10 times more potency than NDGA as a proliferative inhibitor of H-69 small cell lung cancer cells (MaDonal, R. W.; Bunjobpon, W; Liu, T.; Fessler, S.; Pardo, O. E.; Freer, I. K. A.; Glaser, M.; Seckl, M. J.; Robins, D. J.; *Anti-cancer Drug Design*, 2001, 16(6), 261-270). The inventors have invented a novel NDGA derivative based on butane bridge modification designated BB-N, where BB signifies a butane bridge modification, and N signifies NDGA in the following Formula V:

Formula IV

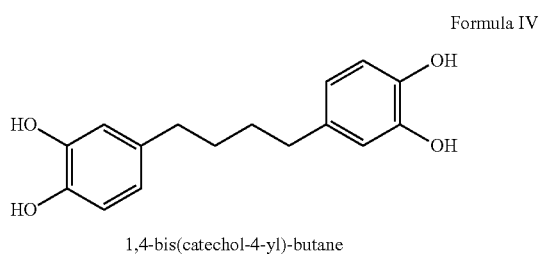

1,4-bis(catechol-4-yl)-butane

Formula V

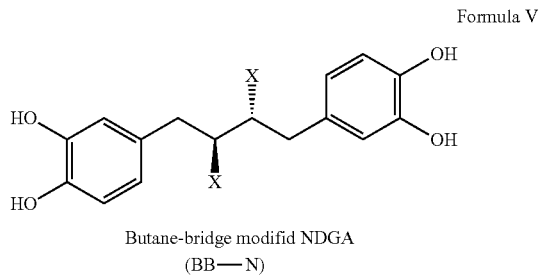

Butane-bridge modifid NDGA
(BB—N)

One aspect of the present invention relates to a butane bridge-modified nordihydroguaiaretic acid derivative compound designated "BB-N", having the foregoing general structure (Formula V), as well as its pharmaceutically acceptable salts.

In the compound of Formula V, each X is selected from the group consisting of —CHO, —CN, —CH$_2$Cl, —CH$_2$Br and —CH$_2$F. However, where the BB-N derivative is used as an intermediate to make the "BB-Sb$_4$N" derivative disclosed below, X may also be H or —CH$_2$CH$_3$, in which case, the designation "X" will be replaced in the appropriate formulas by "Z".

Another aspect of the present invention relates to a butane bridge modified tetra-O-substituted nordihydroguaiaretic acid derivative compound designated "BB-Sb$_4$N", having the following general structure (Formula VI), as well as its pharmaceutically acceptable salts:

Formula VI

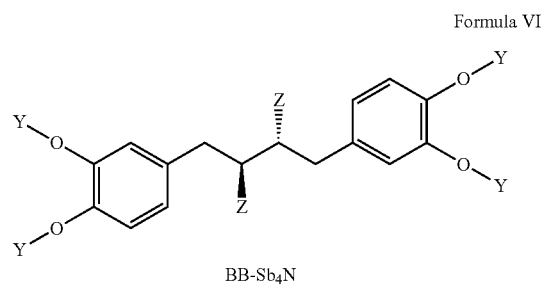

BB-Sb$_4$N

In the designation "BB-Sb$_4$N", "BB" signifies the butane bridge modification aspect of the NDGA base component N and "Sb$_4$N" signifies the tetra-O-substituted nordihydroguaiaretic acid aspect of the bridge modified tetra-O-substituted nordihydroguaiaretic acid derivative compound of the present invention. The compound contains two catechol units, a butane bridge, and a four groups Y, each substituted for H in the NDGA hydroxyl groups (sometimes referred to as the "substituted group Y") designated by "Sb$_4$" in "Sb$_4$N."

The butane bridge links the two catechol units at the 1,4-positions through the 4-position at the phenyl rings of the catechol units. The substituents (Z) at the 2,3-positions of the butane bridge are selected from the group consisting of H, —CHO, —CN, —CH$_2$CH$_3$, —CH$_2$Cl, —CH$_2$Br and —CH$_2$F.

Y is selected from the group consisting of:
-A-R;
—(CH$_2$)$_x$Hal, where x is an integer of 1 to 10, and Hal is a halogen atom, namely any of chlorine, fluorine, bromine or iodine;
—(CH$_2$CH$_2$O)$_y$H, where y is an integer of 1 to 10; and
a carbamate-bonded group selected from the group consisting of:

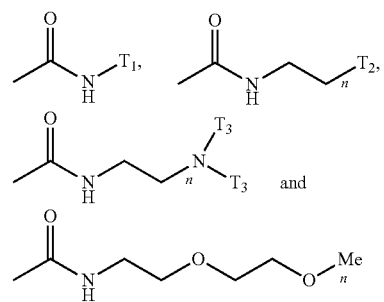

where n is an integer of 1 to 6, T$_1$ is a saturated linear hydrocarbon chain of 2-6 carbons and optionally 1-3 halogen atoms, T$_2$ is a 5- to 7-member ring optionally containing 0-3 double bonds and optionally containing 1-3 atoms of any of O, N and S, and T$_3$ is methyl or ethyl.

When Y is -A-R, R is an end group and A is a linear saturated hydrocarbon side chain with optional heteroatoms that is bonded at one end to the respective hydroxy residue O groups by an ether bond or a carbamate bond and at the other end to a carbon or a heteroatom in the end group R.

The side chain A is selected from the group consisting of a C$_2$-C$_{16}$ linear saturated hydrocarbon chain, optionally with 1-5 heteroatoms selected from the group consisting of O, N and S, bonded to the respective hydroxy residue O groups of NGDA through an ether bond; and 1-5 units of a polyethylene glycol (PEG) chain.

The end group R is selected from the group consisting of:

a 5- to 7-member carbocyclic ring selected from the group consisting of a fully saturated ring with 1 to 3 N, O or S heteroatoms; a ring containing 1 to 3 double bonds for a 6- or 7-member ring and 1 to 2 double bonds for a 5-member ring, with 1 to 3 N, O or S heteroatoms for the 5 to 7 member ring; a ring containing a carbamate bond, a urea bond, a carbonate bond or an amide bond; and a water soluble group selected from the group consisting of an alkali metal salt of sulfonic acid; an alkali metal salt of phosphonic acid; a pharmaceutically acceptable salt; a sugar and a polyhydroxy group.

Another aspect of the invention is a composition comprising the BB-N compound or the BB-Sb$_4$N compound and a pharmaceutically acceptable carrier, optionally with other pharmaceutically acceptable excipients.

Still another aspect of the invention is a method of making the BB-N compound or the BB-Sb$_4$N compound as set forth hereinafter.

Another aspect of the invention is a method of administering to a subject, an amount of either of the BB-N compound or the BB-Sb$_4$N compound alone or as part of a pharmaceutical composition effective prophylactically or for treating a viral infection.

Yet another aspect of the invention is a method of administering to a subject an amount of either the BB-N compound or the BB-Sb$_4$N compound alone or as part of a pharmaceutical composition effective prophylactically or for treating a proliferative disease.

Another aspect of the invention is a method of administering to a subject an amount of either the BB-N compound or the BB-Sb$_4$N compound alone or as part of a pharmaceutical composition effective prophylactically or for treating an inflammatory disease.

Yet another aspect of the invention is a method of administering to a subject an amount of either the BB-N compound or the BB-Sb$_4$N compound alone or as part of a pharmaceutical composition effective prophylactically or for treating a metabolic disease.

A further aspect of the invention is a method of administering to a subject an amount of either the BB-N compound or the BB-Sb$_4$N compound alone or as part of a pharmaceutical composition effective prophylactically or for treating a vascular disease.

Still another aspect of the present invention is a kit comprising a pharmaceutical composition comprising either the BB-N compound or the BB-Sb$_4$N compound and instructions for its use prophylactically or for treating a viral infection, a proliferative disease, an inflammatory disease, a metabolic disease or a vascular disease.

DETAILED DESCRIPTION OF THE INVENTION

As noted above, the present invention relates to nordihydroguaiaretic acid derivative compounds, pharmaceutical compositions containing them, methods of making them, and methods of using them and kits including them for the treatment of diseases and disorders, in particular, viral infections, such as, for example and without limitation, infections caused by human immunodeficiency virus (HIV), human papillomaviruses (HPV)(all subtypes), herpes simplex virus 1 and 2 (HSV-1 and HSV-2), Varicella Zoster virus, cytomegalovirus, Epstein Barr virus, pox viruses (smallpox, cowpox, monkeypox, vaccinia), orthohepadnavirus, JC virus, and BK virus; inflammatory diseases, such as, for example and without limitation, various types of arthritis and inflammatory bowel diseases; metabolic diseases, such as, for example and without limitation, diabetes; vascular diseases, such as for example hypertension, cardiovascular diseases and macular degeneration; and proliferative diseases such as various types of cancers.

The present invention is based on considerations including experience with agents used for treating cancer and viruses, including HIV; derivatives having a chemical structure related to NDGA; where such derivatives have more potency, better PD/PK profile and less or no side effects versus (tetra-O-methyl)nordihydroguaiaretic acid (M$_4$N) (terameprocol), at least some formulations of which are orally bioavailable. The NDGA derivatives of the present invention are in the meso form without any possible mixtures of their enantiomers, which will make the chemical and biological characterization easier. The substituent functional groups for the modifications of the NDGA parent compound are selected from among the most common chemical groups used for successful drug molecule modifications. They are readily able to be synthesized and readily formulated with reasonable aqueous solubility, in that in the HCl or other salt form or in free base, they have considerable aqueous solubility. Other of the NDGA derivatives of the present invention are hydrophobic. The NDGA derivatives of the present invention have good stability, whether they are water soluble compound or hydrophobic compounds. The derivatives may be scaled-up readily for commercial production.

The NDGA derivatives of the present invention were developed based on the fact that NDGA is natural compound with a broad range of biological activities. NDGA has a lot of side effects, which are overcome by the derivatives of the invention. Butane-bridge modified NDGA (BB-N) derivatives, such as 1,4-bis(catechol-4-yl)-butane, possess better biological activities than NDGA. The derivatives have improved biological activities. The research leading to the development of the present invention has also shown that hydroxy group modification of NDGA derivatives, such as M$_4$N, prevents tumor cell replication and selectively induces tumor cell death (apoptosis). This is achieved by preventing Sp1-regulated production of cdc2 (p34) and survivin. Survivin is an inhibitor of apoptosis protein (IAP) over-expressed in pre-cancerous and cancerous cells, and rarely found in healthy adult cells. M$_4$N also prevents proliferation of human immunodeficiency virus (HIV), herpes simplex virus (HSV), and human papilloma virus (HPV). This is achieved through the deactivation of viral Sp1-dependent promoters that are essential for viral propagation. BB-Sb$_4$N derivatives of the present invention will remarkably improve their activities to prevent Sp1-regulated production of cdc2 and survivin by using a suitable functional group to modify the hydroxyl group of NDGA.

Definitions

A "buffer" suitable for use herein includes any buffer conventional in the art, such as, for example, Tris, phosphate, imidazole, and bicarbonate.

A "cyclodextrin" as used herein means an unmodified cyclodextrin or a modified cyclodextrin, and includes without limitation α-cyclodextrin, β-cyclodextrin, γ-cyclodextrin and any modified cyclodextrins containing modifications thereto, such as hydroxypropyl-β-cyclodextrin ("HP-β-CD") or sulfobutyl ether β-cyclodextrin ("SBE-β-CD"). Cyclodextrin typically has 6 (α-cyclodextrin), 7 (β-cyclodextrin), and 8 (γ-cyclodextrin) sugars, up to three substitutions per sugar, and 0 to 24 primary substitutions are therefore possible (primary substitutions are defined as substitutions connected directly to the cyclodextrin ring). The modified or unmodified cyclodextrins used in the present invention may have any appropriate number and location of primary substitutions or other modifications.

An "NDGA derivative" of the present invention as used herein means a derivative of NDGA designated as "BB-N" or "BB-Sb$_4$N" hereinafter.

A "pharmaceutically acceptable carrier" refers to a non-toxic solid, semisolid or liquid filler, diluent, encapsulating material or formulation auxiliary of any conventional type. A "pharmaceutically acceptable carrier" is non-toxic to recipients at the dosages and concentrations employed, and is compatible with other ingredients of the formulation. For example, the carrier for a formulation containing the present catecholic butane or NDGA derivatives preferably does not include oxidizing agents and other compounds that are known to be deleterious to such derivatives. Suitable carriers include, but are not limited to, water, dextrose, glycerol, saline, ethanol, buffer, dimethyl sulfoxide, Cremaphor EL, and combinations thereof. The carrier may contain additional agents such as wetting or emulsifying agents, or pH buffering agents. Other materials such as anti-oxidants, humectants, viscosity stabilizers, and similar agents may be added as necessary.

A "pharmaceutically acceptable salt" as used herein includes the acid addition salts (formed with the free amino groups of the polypeptide) and which are formed with inorganic acids such as, for example, hydrochloric or phosphoric acids, or such organic acids as acetic, mandelic and oxalic acids. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, and histidine. Non-limiting examples of pharmaceutically acceptable salts of the NDGA derivatives of the present invention include, for instance, the following general formula of salts:

[Sb$_4$(BB-N)]·k[acid], where BB-N is butane-bridge modified NDGA, Sb is a substituted group as described in Table 1 and 2, k is an integer or non integer number, and acid is organic or inorganic acid, as exemplified in the following non-limiting Table A:

TABLE A

| Sb | Acid | k |
|---|---|---|
| Containing one basic nitrogen atom | HCl, HBr, HNO$_3$, MeSO$_3$H, H$_2$SO$_4$, aspartic acid, citric acid, benzenesulfonic acid, camphoric acid, camphorsulfonic acid, ethanesulfonic acid, 2-hydroxyethansulfonic acid, formic acid, fumaric acid, galactaric acid, D-gluconic acid, glycolic acid, hippuric acid, L-lactic acid, maleic acid, malic acid, malonic acid, nicotinic acid, palmitic acid, pamoic acid, phosphoric acid, salicylic acid, succinic acid, tartaric acid, p-toluenesulfonic acid. | 1-4 |
| Containing two basic nitrogen atoms | HCl, HBr, HNO$_3$, MeSO$_3$H, H$_2$SO$_4$, aspartic acid, citric acid, benzenesulfonic acid, camphoric acid, camphorsulfonic acid, ethanesulfonic acid, 2-hydroxyethansulfonic acid, formic acid, fumaric acid, galactaric acid, D-gluconic acid, glycolic acid, hippuric acid, L-lactic acid, maleic acid, malic acid, malonic acid, nicotinic acid, palmitic acid, pamoic acid, phosphoric acid, salicylic acid, succinic acid, tartaric acid, p-toluenesulfonic acid. | 1-8 |

The term "pharmaceutically acceptable excipient" as used herein includes vehicles, adjuvants, or diluents or other auxiliary substances, such as those conventional in the art, which are readily available to the public. For example, pharmaceutically acceptable auxiliary substances include pH adjusting and buffering agents, tonicity adjusting agents, stabilizers, wetting agents and the like.

A "ring" unless otherwise specified, as used herein such as in the terms "5-member ring," "6-member ring" and "7-member ring," refers to a carbocyclic ring with any indicated heteroatoms.

The terms "subject," "host," and "patient," are used interchangeably herein to refer to an animal being treated with the present compositions, including, but not limited to, simians, humans, felines, canines, equines, bovines, porcines, ovines, caprines, mammalian farm animals, mammalian sport animals, and mammalian pets.

A "substantially purified" compound in reference to the NDGA derivatives herein is one that is substantially free of compounds that are not the NDGA derivatives of the present invention (hereafter, "non-NDGA derivative materials"). By substantially free is meant at least 50%, preferably at least 70%, more preferably at least 80%, and even more preferably at least 90% free of non-NDGA derivative materials.

As used herein, the terms "treatment," "treating," and the like, refer to obtaining a desired pharmacologic and/or physiologic effect. The effect may be prophylactic in terms of completely or partially preventing a condition or disease or symptom thereof and/or may be therapeutic in terms of a partial or complete cure for a condition or disease and/or adverse affect attributable to the condition or disease. "Treatment," thus, for example, covers any treatment of a condition or disease in an animal, preferably in a mammal, and more preferably in a human, and includes: (a) preventing the condition or disease from occurring in a subject which may be predisposed to the condition or disease but has not yet been diagnosed as having it; (b) inhibiting the condition or disease, such as, arresting its development; and (c) relieving, alleviating or ameliorating the condition or disease, such as, for example, causing regression of the condition or disease.

This invention is described by way of example only and is not to be interpreted in any way as limiting the invention. Thus, this invention is not limited to particular embodiments described, as such may, of course, vary. It is also to be understood that the terminology used herein is for the purpose of describing particular embodiments only, and is not intended to be limiting, since the scope of the present invention will be limited only by the appended claims in a non-provisional application based on this provisional application.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It must be noted that as used herein, the singular forms "a", "an", and "the" include plural referents unless the context clearly dictates otherwise. Thus, for example, reference to "a derivative" includes a plurality of such derivatives and reference to "the NDGA derivative" includes reference to one or more NDGA derivatives and equivalents thereof known to those skilled in the art.

All publications mentioned herein, including patents, patent applications, and journal articles are incorporated herein by reference in their entireties including the references cited therein, which are also incorporated herein by reference. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As noted above, one aspect of the present invention relates to a butane bridge-modified nordihydroguaiaretic acid derivative compound designated "BB-N", having the general structure (Formula V), as well as its pharmaceutically acceptable salts.

Formula V

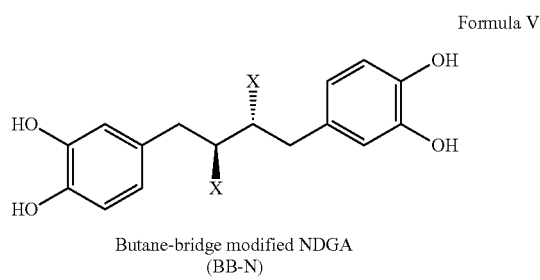

Butane-bridge modified NDGA
(BB-N)

In the compound of Formula V, each X is selected from the group consisting of —CHO, —CN, —CH$_2$Cl, —CH$_2$Br and —CH$_2$F. However, as noted above, where the BB-N derivative is used as an intermediate to make the "BB-Sb$_4$N" derivative disclosed below, X may also be H or —CH$_2$CH$_3$, in which case, the designation "X" will be replaced in the appropriate formulas by "Z".

Another aspect of the present invention relates to a butane bridge modified tetra-O-substituted nordihydroguaiaretic acid derivative compound designated "BB-Sb$_4$N", having the following general structure (Formula VI), as well as its pharmaceutically acceptable salts:

Formula VI

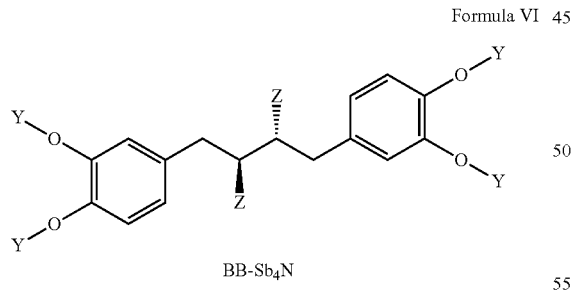

BB-Sb$_4$N

As also noted above, Y is selected from the group consisting of:

-A-R;

—(CH$_2$)$_x$Hal, where x is an integer of 1 to 10, and Hal is a halogen atom, namely any of chlorine, fluorine, bromine or iodine;

—(CH$_2$CH$_2$O)$_y$H, where y is an integer of 1 to 10; and a carbamate-bonded group selected from the group consisting of:

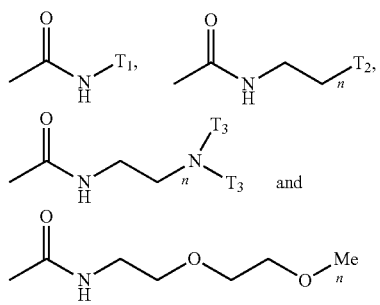

where n is an integer of 1 to 6, T$_1$ is a saturated linear hydrocarbon chain of 2-6 carbons and optionally 1-3 halogen atoms, T$_2$ is a 5- to 7-member ring optionally containing 0-3 double bonds and optionally containing 1-3 atoms of any of O, N and S, and T$_3$ is methyl or ethyl.

Where Y is —(CH$_2$)$_x$Hal, x is preferably 1 to 3, and Hal is chlorine or fluorine; more preferably, in this instance, Y is —(CH$_2$)$_2$F, for example.

Where Y is —(CH$_2$CH$_2$O)$_y$H, y is preferably 1 to 3, and more preferably, for example, in this instance, Y is —(CH$_2$)$_2$OH (when y is 1); or —(CH$_2$)$_2$—O—(CH$_2$)$_2$—OH (when y is 2).

With the foregoing definitions of Y, the butane bridge substituents Z, and their side chains A and end groups R of the substituted Y groups of the BB-Sb$_4$N derivative of NDGA may be selected from those set forth in the Brief Summary of the Invention above, and are also set forth in tabular form in the following Table 1.

TABLE 1

| Z group | —CHO, —CN, —CH$_2$CH$_3$, —CH$_2$Cl, —CH$_2$Br or —CH$_2$F |
|---|---|
| Side chain A | C$_2$-C$_{16}$ linear saturated hydrocarbon chain optionally with 1-5 N, O or S heteroatoms, and the chain is bonded to the respective hydroxy groups residue O groups of the phenyl moieties through an ether bond |
| | 1-5 units of polyethylene glycol (PEG) chain |
| R is a 7 member ring | fully saturated 7-member ring with 1 to 3 N, O or S heteroatoms |
| | 7-member ring containing 1 to 3 double bonds with 1 to 3 N, O or S heteroatoms |
| | 7-member ring containing a carbamate bond, a urea bond, a carbonate bond or an amide bond |
| R is a 6 member ring | fully saturated 6-member ring with 1 to 3 N, O or S heteroatoms |
| | 6-member ring containing 1 to 3 double bonds with 1 to 3 N, O or S heteroatoms |
| | 6-member ring containing a carbamate bond, a urea bond, a carbonate bond or an amide bond |
| R is a 5 member ring | fully saturated 5-member ring with 1 to 3 N, O or S heteroatoms |
| | 5-member ring containing 1 to 2 double bonds with 1 to 3 N, O or S heteroatoms |
| | 5-member ring containing a carbamate bond, a urea bond, a carbonate bond or an amide bond |
| R is a water soluble group | an alkali metal salt of sulfonic acid |
| | an alkali metal salt of phosphonic acid |
| | a pharmaceutically acceptable salt, such as shown in Table A |
| | a sugar |
| | a polyhydroxy group |

Non-limiting examples of a suitable side chain A are C$_2$-C$_4$ linear chain, such as ethylene, propylene or butylene, bonded at one end to the respective hydroxy residue O groups of NDGA through an ether bond; C$_2$-C$_4$ linear chain, such as ethylene, propylene or butylene, with an O or N heteroatom, and the chain is bonded to the respective hydroxy residue O groups of NGDA through an ether bond; 1-3 units of polyethylene glycol (PEG) chain; or a carbamate bond. The side chain is bonded at the other end to a carbon or heteroatom of the end group R.

Nonlimiting examples of suitable Y and R end groups are set forth in the following Table 2:

TABLE 2

| R is 5-7 member carbocyclic ring containing 1-3 N, O or S heteroatoms | 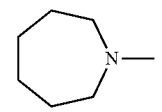 |
|---|---|
| | 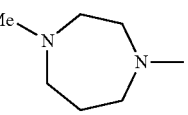 |
| | 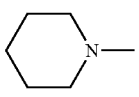 |
| | 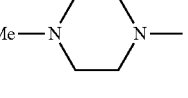 |
| | 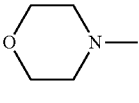 |
| | 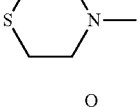 |
| | 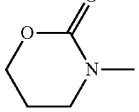 |
| | 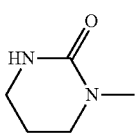 |
| | 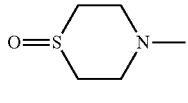 |
| | 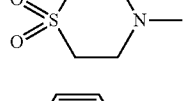 |
| | 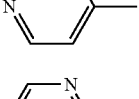 |
| | 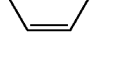 |

TABLE 2-continued

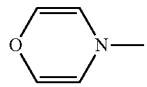

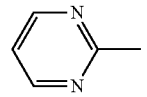

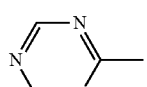

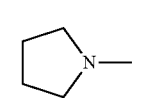

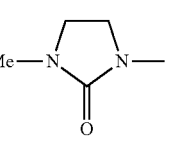

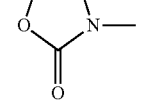

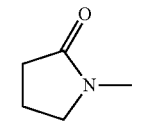

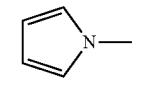

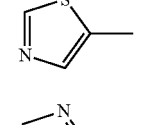

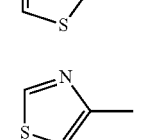

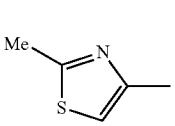

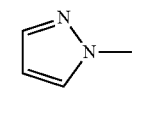

TABLE 2-continued

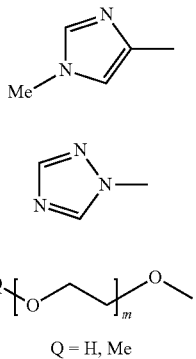

R is polyhydroxy, sugar, or other water soluble group, where m is an integer of 2 to 6

Q = H, Me

Methods to synthesize butane bridge modified NDGA (BB-N) and the butane bridge modified tetra-O-substituted nordihydroguaiaretic acid derivative compound designated (BB-Sb₄N) are as set forth below.

Several methods to synthesize 1,4-bis(catechol-4-yl)-butane, one of starting materials, were reported in the literature (such as by multiple step synthesis, see *Anticancer Drug Design*, 2001, 16, 261-270; and by homo-coupling the corresponding boronic acid, see *Tetrahedron Lett*, 2002, 43, 8149-8151). However, those methods gave low yields of the expected product, and some starting materials are not readily available.

To overcome the deficiencies of the prior synthesis methods, the inventors developed a new method to synthesize the expected 1,4-bis(catechol-4-yl)-butane, which is obtained in remarkably high yield by a simplified procedure.

McMurry coupling an aldehyde to give a mixture of cis- and trans- form compounds, which is reduced to give the expected tetra-O-methyl-BB-N as a precursor for the BB-N derivatives of Formula V:

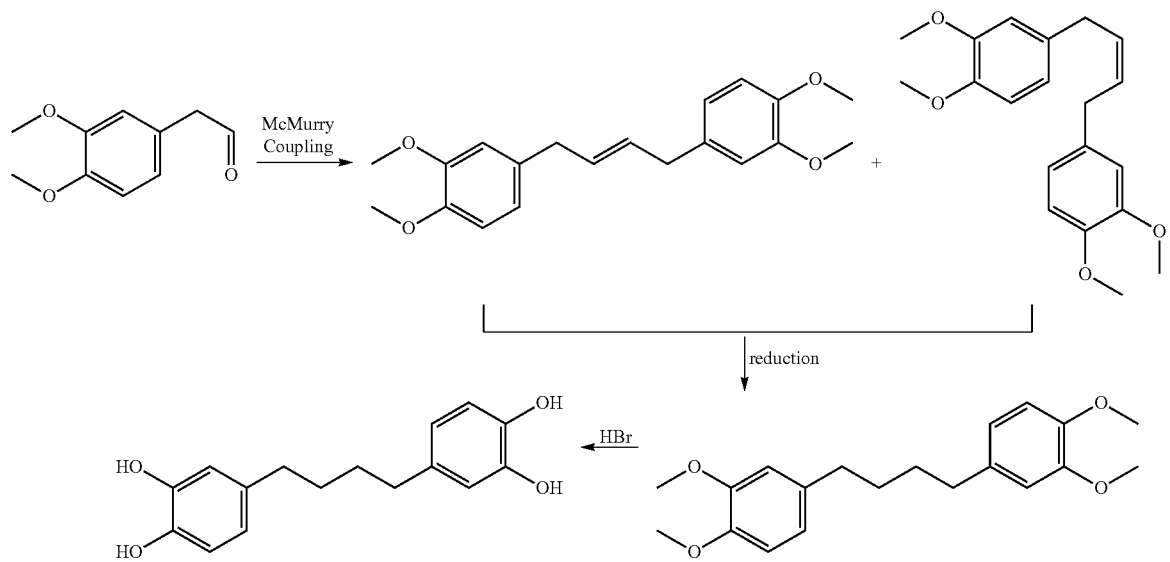

TABLE 2-continued

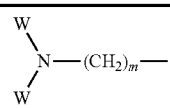

W = Me, Et

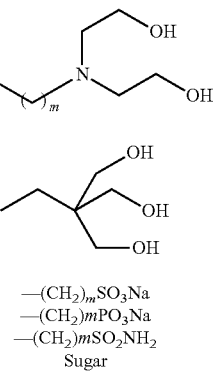

—(CH₂)ₘSO₃Na
—(CH₂)ₘPO₃Na
—(CH₂)ₘSO₂NH₂
Sugar

Other butane bridge substituted 1,4-bis(catechol-4-yl)butanes can be synthesized as follows:

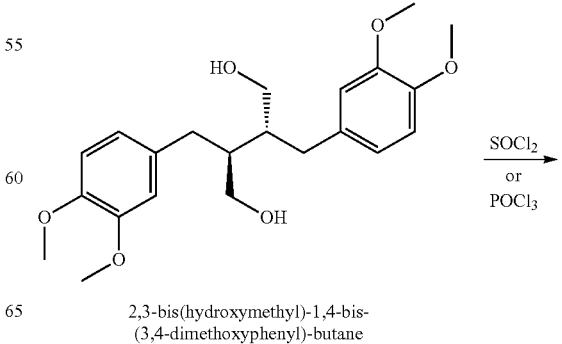

2,3-bis(hydroxymethyl)-1,4-bis-(3,4-dimethoxyphenyl)-butane

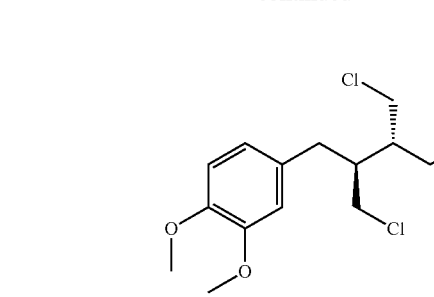

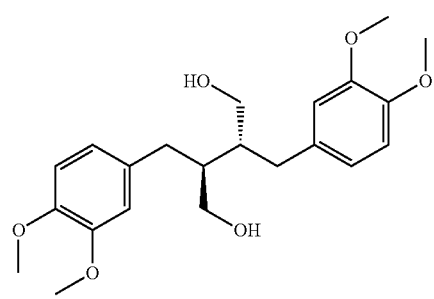

2,3-bis(hydroxymethyl)-1,4-bis-
(3,4-dimethoxyphenyl)-butane

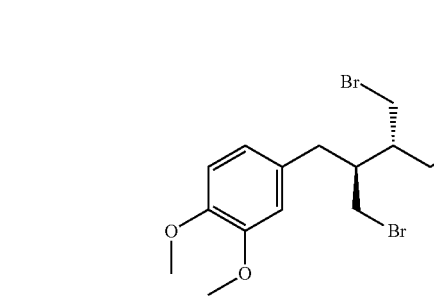

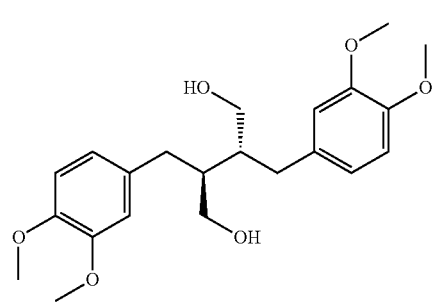

2,3-bis(hydroxymethyl)-1,4-bis-
(3,4-dimethoxyphenyl)-butane

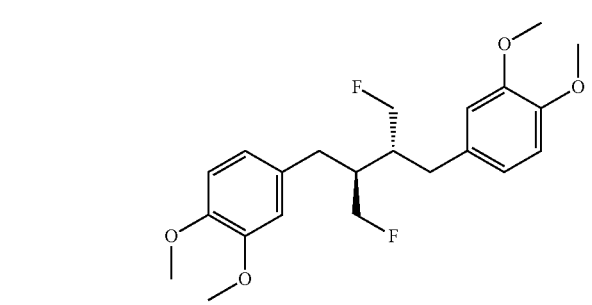

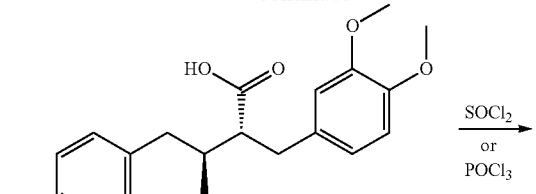

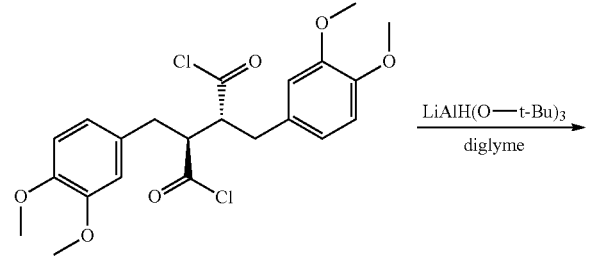

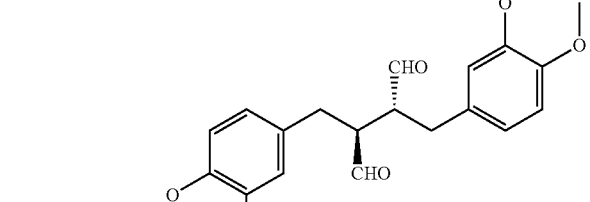

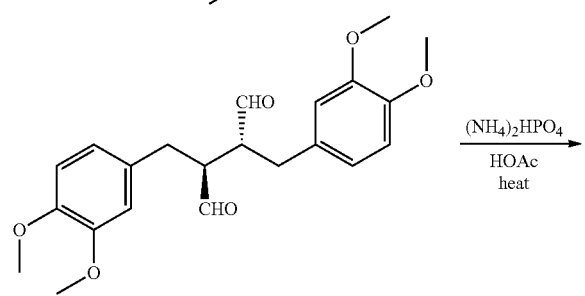

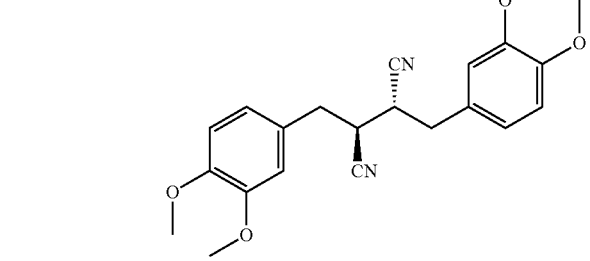

The starting 2,3-bis(hydroxymethyl)-1,4-bis(3,4-dimethoxyphenyl)-butane could be synthesized according to literature (*JACS*, 1957, 79, 3823-3827; *Tetrahedron: Ass.* 1998, 9, 2827-2831; *Tetrahedron* 1996, 52(39), 12799-12814; *Tetrahedron Ass.* 1995, 6(4), 843-844.)

Methods to synthesize the ether bonded butane bridge modified tetra-O-substituted NDGA derivatives BB-Sb₄N (Formula VI) from the butane bridge modified NDGA derivatives BB-N(Formula V, where the X groups are replaced by the Z groups as explained above) are set forth below.

General method 1: reaction of alkyl halide with butane bridge modified NDGA (BB-N) under basic catalytic conditions:

Methods to synthesize carbamate bonded butane bridge modified tetra-O-substituted NDGA derivatives (BB-Sb₄N):

General method 1: reaction of an isocyanate compound with BB-N

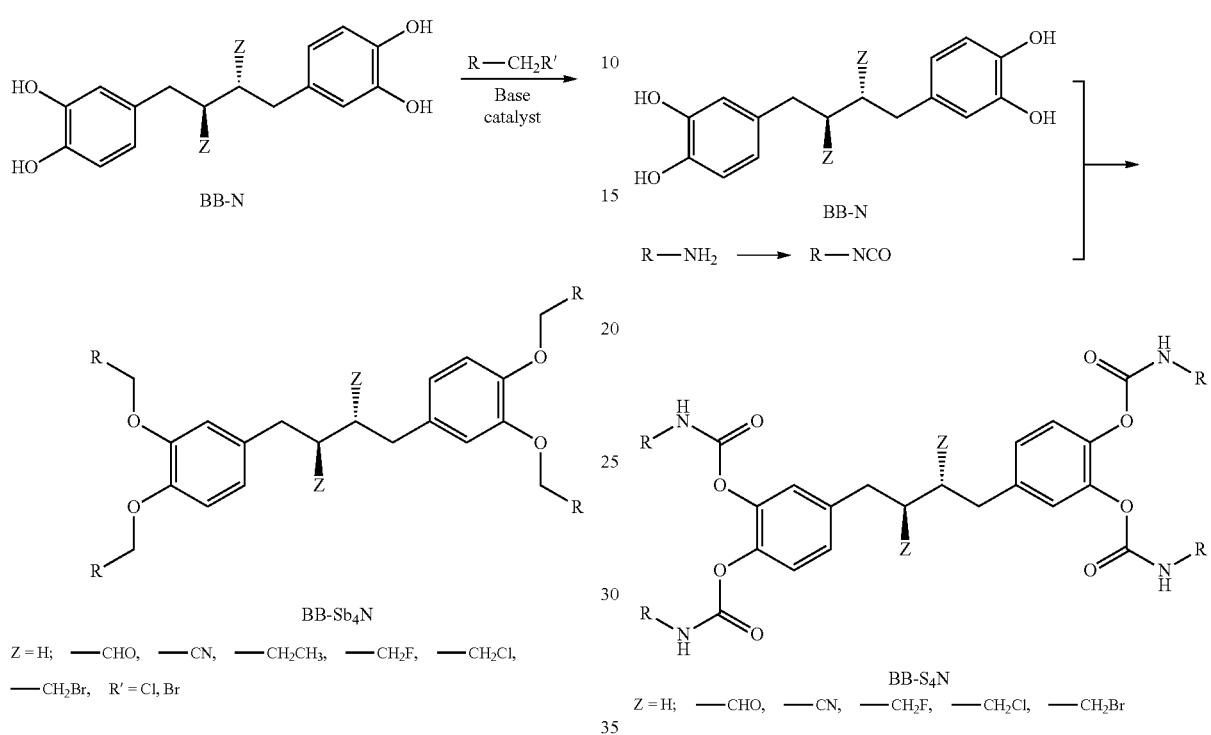

General method 2: reaction of toluenesulfonic acid activated alcohol with butane bridge modified NDGA (BB-N):

General method 2: BB-N is reacted with an activated amino compound

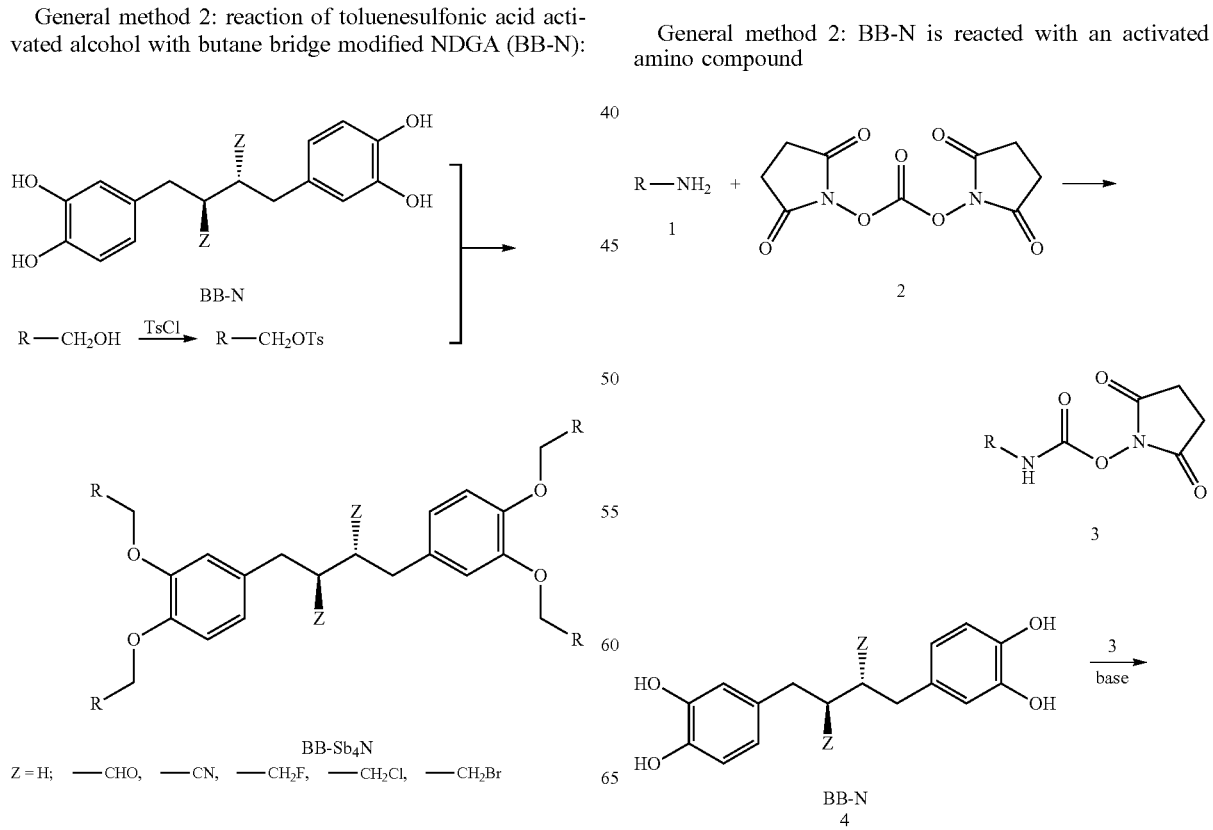

-continued

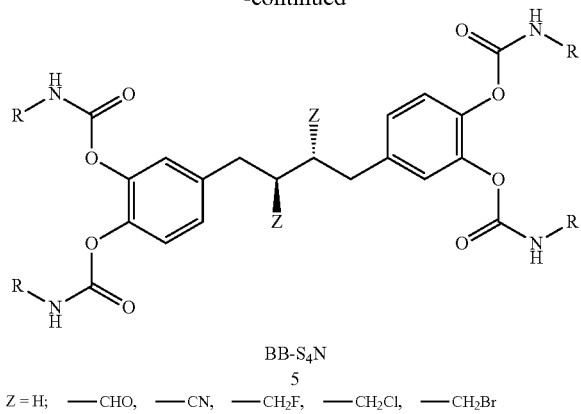

BB-S₄N
5

Z = H; —CHO, —CN, —CH₂F, —CH₂Cl, —CH₂Br

Details of the preparation of specific NDGA derivative compounds BB-N and BB-S₄N according to the present invention will be set forth below in the Examples section.

The present NDGA derivatives in a suitable formulation, preferably but not exclusively as the active ingredient or as one of two or more active ingredients in a pharmaceutical composition with a pharmaceutically acceptable carrier or excipient where appropriate, can be safely administered to a subject in need of such treatment by intranasal delivery, by inhalation, intravenously such as by infusion or by injection into the central vein for example, intra-arterially (with or without occlusion), intraperitoneally, interstitially, subcutaneously, transdermally, intradermally, intraocularly, intramuscularly, topically, intracranially, intraventricularly, orally, or buccally, or by implantation.

Moreover, the NDGA derivatives can be safely administered to a subject in need of such treatment in solution, suspension, semisolid or solid forms as appropriate, or in liposomal formulations, nanoparticle formulations, or micellar formulations for administration via one or more routes mentioned above.

Furthermore, the NDGA derivatives in liposomal formulations, nanoparticles formulations, or micellar formulations can be embedded in a biodegradable polymer formulation and safely administered, such as by subcutaneous implantation.

Compositions for administration herein may, be in any suitable form, such as and without limitation, a solution, suspension, tablet, pill, capsule, sustained release formulation or powder, a liquid that is either hydrophilic or hydrophobic, a powder such as one resulting from lyophilization, an aerosol, an aqueous or water-soluble composition, a hydrophobic composition, a liposomal composition, a micellar composition such as that based on Tween® 80 or diblock copolymers, a nanoparticle composition, a polymer composition, a cyclodextrin complex composition, an emulsion, or as lipid based nanoparticles termed "lipocores."

The present invention further encompasses compositions, including pharmaceutical compositions, comprising the NDGA derivatives and pharmaceutically acceptable carriers or excipients. These compositions may include a buffer, which is selected according to the desired use of the NDGA derivatives, and may also include other substances appropriate for the intended use. Those skilled in the art can readily select an appropriate buffer, a wide variety of which are known in the art, suitable for an intended use, in view of the present disclosure. In some instances, the composition can comprise a pharmaceutically acceptable excipient, a variety of which are known in the art. Pharmaceutically acceptable excipients suitable for use herein are described in a variety of publications, including, for example, Gennaro (Gennaro, A., *Remington: The Science and Practice of Pharmacy*, 19th edition, Lippincott, Williams, & Wilkins, (1995)); Ansel, et al. (Ansel, H. C. et al., *Pharmaceutical Dosage Forms and Drug Delivery Systems*, 7$^{th}$ edition, Lippincott, Williams, & Wilkins (1999)); and Kibbe (Kibbe, A. H., *Handbook of Pharmaceutical Excipients*, 3$^{rd}$ edition Amer. Pharmaceutical Assoc.).

The compositions herein are formulated in accordance to the mode of potential administration. Thus, if the composition is intended to be administered intranasally or by inhalation, for example, the composition may be a converted to a powder or aerosol form, as conventional in the art, for such purposes. Other formulations, such as for oral or parenteral delivery, are also used as conventional in the art.

Compositions or formulations suitable for oral or injectable delivery additionally includes a pharmaceutical composition containing a catecholic butane for treatment of the indicated diseases where the composition is formulated with a pharmaceutically acceptable carrier and other optional excipients, wherein the carrier comprises at least one of a solubilizing agent and an excipient selected from the group consisting of: (a) a water-soluble organic solvent; (b) a cyclodextrin (including a modified cyclodextrin); (c) an ionic, non-ionic or amphipathic surfactant, (d) a modified cellulose; (e) a water-insoluble lipid; and a combination of any of the carriers (a)-(e).

The water-soluble organic solvent may be preferably, but not necessarily, other than dimethyl sulfoxide. Non-limiting exemplary water-soluble organic insolvents include polyethylene glycol ("PEG"), for example, PEG 300, PEG 400 or PEG 400 monolaurate, propylene glycol ("PG"), polyvinyl pyrrolidone ("PVP"), ethanol, benzyl alcohol or dimethylacetamide.

The cyclodextrin or modified cyclodextrin may be, without limitation, α-cyclodextrin, β-cyclodextrin, γ-cyclodextrin, HP-β-CD or SBE-β-CD.

The ionic, non-ionic or amphipathic surfactant may include, for example without limitation, a surfactant such as polyoxyethylene sorbitan monolaurate (also known as polysorbate), which is a non-ionic surfactant, for example, polysorbate 20 and polysorbate 80, commercially available as Tween® 20 or Tween® 80, d-alpha-tocopheryl polyethylene glycol 1000 succinate ("TPGS"), glycerol monooleate (also known as glyceryl monooleate), an esterified fatty acid or a reaction product between ethylene oxide and castor oil in a molar ratio of 35:1, commercially available as Cremophor® EL. Preferably, for certain embodiments, when the surfactant is a non-ionic surfactant, the non-ionic surfactant is present in the absence of xanthan gum.

Non-limiting examples of a modified cellulose include ethyl cellulose ("EC"), hydroxylpropyl methylcellulose ("HPMC"), methylcellulose ("MC") or carboxy methylcellulose ("CMC"). In one embodiment of the invention, the catecholic butane may be solubilized in modified celluloses that can be diluted in ethanol ("EtOH") prior to use.

The water-insoluble lipids include, for example, an oil or oils, such as castor oil, sesame oil or peppermint oil, a wax or waxes, such as beeswax or carnuba wax, and mixed fat emulsion compositions such as Intralipid® (Pharmacia & Upjohn, now Pfizer), used as per the manufacturer's recommendation. For example, adult dosage is recommended to be not exceeding 2 g of fat/kg body weight/day (20 mL, 10 mL and 6.7 mL/kg of Intralipid® 10%, 20% and 30%, respectively). Intralipid® 10% is believed to contain in 1,000 mL: purified soybean oil 100 g, purified egg phospholipids 12 g, glycerol anhydrous 22 g, water for injection q.s. ad 1,000 mL. pH is adjusted with sodium hydroxide to pH approximately 8. Intralipid® 20% contains in 1,000 mL: purified soybean oil 200 g, purified egg phospholipids 12 g, glycerol anhydrous 22 g, water for injection q.s. ad 1,000 mL. pH is adjusted with sodium hydroxide to pH approximately 8. Intralipid® 30% contains in 1,000 mL: purified soybean oil 300 g, purified egg phospholipids 12 g, glycerol anhydrous 16.7 g, water for injection q.s. ad 1,000 mL. pH is adjusted with sodium hydroxide to pH approximately 7.5. These Intralipid® products are stored at controlled room temperature below 25° C. and should not be frozen.

In one embodiment of the invention, the NDGA derivative is dissolved or dissolved and diluted in different carriers to form a liquid composition for oral administration into animals, including humans. For example, in one aspect of this embodiment, the NDGA derivative is dissolved in a water-soluble organic solvent such as a PEG 300, PEG 400 or a PEG 400 monolaurate (the "PEG compounds") or in PG. In another embodiment, the NDGA derivative is dissolved in a modified cyclodextrin, such as HP-β-CD or SBE-β-CD. In yet another embodiment, the present NDGA derivative is solubilized and/or diluted in a combination formulation containing a PEG compound and HP-β-CD. In a further embodiment, the NDGA derivative herein is dissolved in a modified cellulose such as HPMC, CMC or EC. In yet another embodiment, the NDGA derivative herein is dissolved in another combination formulation containing both a modified cyclodextrin and modified cellulose, such as, for example, HP-β-CD and HPMC or HP-β-CD and CMC.

In yet another embodiment, the NDGA derivative is dissolved in ionic, non-ionic or amphipathic surfactants such as Tween® 20, Tween® 80, TPGS or an esterified fatty acid. For example, the present compounds can be dissolved in TPGS alone, or Tween® 20 alone, or in combinations such as TPGS and PEG 400, or Tween® 20 and PEG 400.

In a further embodiment, the present NDGA derivative is dissolved in a water-insoluble lipid such as a wax, fat emulsion, for example Intralipid®, or oil. For example, the present compounds can be dissolved in peppermint oil alone, or in combinations of peppermint oil with Tween® 20 and PEG 400, or peppermint oil with PEG 400, or peppermint oil with Tween® 20, or peppermint oil with sesame oil.

Of course, EC may be substituted or added in place of the HPMC or CMC in the foregoing examples; PEG 300 or PEG 400 monolaurate can be substituted or added in place of PEG 400 in the foregoing examples; Tween® 80 may be substituted or added in place of Tween® 20 in the foregoing examples; and other oils such as corn oil, olive oil, soybean oil, mineral oil or glycerol, may be substituted or added in place of the peppermint oil or sesame oil in the foregoing examples.

Further, heating may be applied, for example, heating to a temperature of about 30° C. to about 90° C., in the course of formulating any of these compositions to achieve dissolution of the compounds herein or to obtain an evenly distributed suspension of the NDGA derivative.

In still a further embodiment, the NDGA derivative may be administered orally as a solid, either without any accompanying carrier or with the use of carriers. In one embodiment, the NDGA derivative is first dissolved in a liquid carrier as in the foregoing examples, and subsequently made into a solid composition for administration as an oral composition. For example, the NDGA derivative is dissolved in a modified cyclodextrin such as HP-β-CD, and the composition is lyophilized to yield a powder that is suitable for oral administration.

In a further embodiment, the NDGA derivative is dissolved or suspended in a TPGS solution, with heating as appropriate to obtain an evenly distributed solution or suspension. Upon cooling, the composition becomes creamy and is suitable for oral administration.

In yet another embodiment, the NDGA derivative is dissolved in oil and beeswax is added to produce a waxy solid composition.

In general, in preparing the oral formulations, the NDGA derivative herein is first solubilized before other excipients are added so as to produce compositions of higher stability. Unstable formulations are not desirable. Unstable liquid formulations frequently form crystalline precipitates or biphasic solutions. Unstable solid formulations frequently appear grainy and clumpy and sometimes contain runny liquids. An optimal solid formulation appears smooth, homogenous, and has a small melting temperature range. In general, the proportions of excipients in the formulation may influence stability. For example, too little stiffening agent such as beeswax may leave the formulation too runny for an elegant oral formulation.

Hence, in general, for the liquid formulations of the present invention, the excipients used should be good solvents of the NDGA derivative herein. In other words, the excipients should be able to dissolve the NDGA derivative without heating. The excipients should also be compatible with each other independent of the NDGA derivative such that they can form a stable solution, suspension or emulsion. Also, in general, for the solid formulations of the present invention, the excipients used should also be good solvents of the NDGA derivative to avoid clumps and non-uniform formulations. To avoid solid formulations that are too runny or heterogeneous in texture, which are undesirable, the excipients should be compatible with each other such that they form a smooth homogeneous solid, even in the absence of the NDGA derivative.

The present invention further relates to a method of producing the pharmaceutical composition of the present invention, the method involving making or providing the NDGA derivative in a substantially purified form, combining the composition with a pharmaceutically acceptable carrier or excipient, and formulating the composition in a manner that is compatible with the mode of desired administration.

The compounds and compositions of the present invention find use as therapeutic agents in situations, for example, where one wishes to provide a treatment to a subject who has a proliferative disease such as a malignant, premalignant or benign tumor, a viral disease, an inflammatory disease, a metabolic disease or a vascular disease.

The compounds and compositions of the present invention can be used to treat a variety of tumors and cancers, including, without limitation, hematological malignancies such as leukemia, for instance acute or chronic lymphoblastic leukemia, acute or chronic myeloid leukemia, acute or chronic lymphocytic leukemia, acute or chronic myelogenous leukemia, childhood acute leukemia, chronic lymphocytic leukemia, hairy cell leukemia, malignant cutaneous T-cells, mycosis fungoides, non-malignant fibrous cutaneous T-cell lymphoma, lymphomatoid papulosis, T-cell rich cutaneous lymphoid hyperplasia, non-Hodgkin's lymphoma, Hodgkin's lymphoma, bullous pemphigoid, discoid lupus erythematosus, lichen planus, adrenocortical carcinoma, anal cancer, bile duct cancer, bladder cancer, bone cancer, osteosarcoma/malignant fibrous histiocytoma, neurological tumors and malignancies such as neuroblastoma, glioblastoma, astrocytoma, gliomas, brain stem glioma, brain tumor ependymoma, medulloblastoma, female and male breast cancer, carcinoid tumor gastrointestinal, carcinoma adrenocortical, carcinoma islet cell, clear cell cancer, clear cell sarcoma of tendon sheaths, colon cancer, colorectal cancer, cutaneous T-cell lymphoma, endometrial cancer, esophageal cancer, Ewing's family of tumors, extragonadal germ cell tumor, extrahepatic bile duct cancer, eye cancer, intraocular melanoma, ductal cancer, eye cancer retinoblastoma, dysplastic oral mucosa, invasive oral tumor, gallbladder cancer, gastric (stomach) cancer, gastrointestinal carcinoid tumor, germ cell tumor extragonadal, germ cell tumor, gestational trophoblastic tumor, hepatocellular (liver) cancer, hypopharyngeal cancer, intraocular melanoma, islet cell carcinoma (endocrine pancreas), Kaposi's sarcoma, laryngeal cancer, liver cancer, lung tumors and cancers such as non-small cell lung cancer and small cell lung cancer, malignant mesothelioma, melanoma, merkel cell carcinoma, multiple endocrine neoplasia syndrome, mycosis fungoides, multiple myeloma, nasal cavity tumors, paranasal and sinus cancer, nasopharyngeal cancer, oral cavity and lip cancer, oropharyngeal cancer, pancreatic cancer, parathyroid cancer, penile cancer, pheochromocytoma, pineal and supratentorial primitive neuroectodermal tumors, pituitary tumor, pleuropulmonary blastoma, prostate cancer, rectal cancer, renal, pelvis and ureter transitional cell cancer, retinoblastoma, rhabdomyosarcoma, salivary gland cancer, sarcoma soft tissue adult, Sezary syndrome, skin cancer, small intestine cancer, testicular tumors and cancer, thymoma, thyroid cancer, urethral cancer, transitional and squamous cell urinary carcinoma, gynecological tumors and cancer such as cervical cancer, ovarian tumors and cancer, ovarian epithelial cancer, ovarian germ cell tumor, uterine cancer, endometrial cancer, vaginal cancer, vulvar cancer, Waldenström's macroglobulinemia, Wilms' tumor, liver tumors including hepatocellular carcinoma ("HCC") and tumors of the biliary duct, other lung tumors including small cell and clear cell cancers, sarcomas in different organs; as well as other cancers and tumors.

Non limiting examples of viral diseases that may be treated effectively by the NDGA derivatives of the present invention, include for example and without limitation viral infections caused by human immunodeficiency virus (HIV), human papillomaviruses (HPV)(all subtypes), herpes simplex virus 1 and 2 (HSV-1 and HSV-2), Varicella Zoster virus, cytomegalovirus, Epstein Barr virus, pox viruses (smallpox, cowpox, monkeypox, vaccinia), orthohepadnavirus, JC virus, and BK virus, among others.

Non-limiting examples of inflammatory diseases that may be treated effectively by the NDGA derivatives of the present invention include, for instance and without limitation, rheumatoid arthritis, osteoarthritis, psoriasis, sarcoidosis, systemic lupus erythematosis, Stills disease, cystic fibrosis, chronic obstructive pulmonary disease and inflammatory bowel diseases such as ulcerative colitis and Crohns, among others.

Non-limiting examples of metabolic diseases that may be treated effectively by the NDGA derivatives of the present invention include, for instance, diabetes mellitus (juvenile onset and adult onset), diabetes insipidis, syndrome X, hyperlipidemia, hypercholesterolemia, hypoglycemia, atheroma, ketoacidosis, Addisons disease, Cushings syndrome, hyperparathyroidism, hyperthyroidism, leucodystrophy and porphyria, among others.

Non-limiting examples of vascular diseases that may be treated effectively by the NDGA derivatives of the present invention include, for instance and without limitation, arterial hypertension, pulmonary arterial hypertension, cardiovascular disease and macular degeneration, among others.

As mentioned above, an effective amount of the NDGA derivative is administered to the host, where "effective amount" means a dosage sufficient to produce a desired result. In some embodiments, the desired result is at least a reduction in one or more symptoms of the viral infection or the inflammatory, metabolic or proliferative disease. Typically, the compositions of the present invention will contain from less than about 0.1% up to about 99% of the active ingredient, that is, the NDGA derivative herein; optionally, the present invention will contain about 5% to about 90% of the active ingredient. The appropriate dose to be administered depends on the subject to be treated, such as the general health of the subject, the age of the subject, the state of the disease or condition, the weight of the subject, for example. Generally, about 0.1 mg to about 500 mg may be administered to a child and about 0.1 mg to about 5 grams may be administered to an adult. The NDGA derivative can be administered in a single or, more typically, multiple doses. Preferred dosages for a given agent are readily determinable by those of skill in the art by a variety of means in view of the present disclosure. Other effective dosages can be readily determined by one of ordinary skill in the art in view of the present disclosure through routine trials establishing dose response curves. The amount of NDGA derivative will, of course, vary depending upon the particular NDGA derivative used, as well as the nature of the formulation containing the NDGA derivative, and the route of administration.

The frequency of administration of the NDGA derivative, as with the doses, will be determined by the care giver based on age, weight, disease status, health status and patient responsiveness. Thus, the agents may be administered one or more times daily or as appropriate for as long as needed as conventionally determined.

Kits with multiple or unit doses of the NDGA derivative are included in the present invention. In such kits, in addition to the containers containing the multiple or unit doses of the compositions containing the NDGA derivative will be instructions for its use for a given indication such as an informational sheet or package insert with instructions describing the use and attendant benefits of the drugs in treating the pathological condition of interest, such as any of a number of inflammatory, metabolic, vascular or proliferative diseases or a viral infection.

The present invention will now be described in greater detail with reference to the following specific, non-limiting working examples, except as noted where the examples are indicated as being prophetic.

General Procedure.

All reactions were carried out in oven-dried glassware (120° C.) under an atmosphere of nitrogen, unless as indicated otherwise. Acetone, dichloromethane, 1,4-dioxane, ethyl acetate, hexane, and tetrahydrofuran were purchased Mallinckrodt Chemical Co. Acetone was dried with 4 Å molecular sieves and distilled. Dichloromethane, ethyl acetate, and hexane were dried and distilled from $CaH_2$. 1,4-Dioxane and tetrahydrofuran were dried by distillation from sodium and benzophenone under an atmosphere of nitrogen. Nordihydroguaiaretic acid was purchased from Fluka Chemical Co. 4-(2-Chloroethyl)morpholine hydrochloride, 4-(3-chloropropyl)morpholine hydrochloride, 1-(3-chloropropyl)piperidine monohydrochloride, 1-(2-chloroethyl)piperidine monohydrochloride, 2-chloroethanol, (2-chloroethoxy)ethene, 1-(2-chloroethyl)pyrrolidine hydrochloride, N,N'-dicyclohexylcarbodiimide (DCC), 4-dimethylaminopyridine (DMAP), and potassium carbonate were purchased from Aldrich Chemical Co.

The melting point was obtained with a Buchi 535 melting point apparatus. Analytical thin layer chromatography (TLC) was performed on precoated plates (silica gel 60 F-254), purchased from Merck Inc. Gas chromatographic analyses were performed on a Hewlett-Packard 5890 Series II instrument equipped with a 25-m crosslinked methyl silicone gum capillary column (0.32 mm i.d.). Nitrogen gas was used as a carrier gas and the flow rate was kept constant at 14.0 mL/min. The retention time $t_R$ was measured under the following conditions: injector temperature 260° C., isothermal column temperature 280° C. Gas chromatography and low resolution mass spectral analyses were performed on a Agilent Technology 6890N Network GC System equipped with a Agilent 5973 Network Mass Selective Detector and capillary HP-1 column. Purification by gravity column chromatography was carried out by use of Merck Reagents Silica Gel 60 (particle size 0.063-0.200 mm, 70-230 mesh ASTM). Purity of all compounds was >99.5%, as checked by HPLC or GC.

Ultraviolet (UV) spectra were measured on a Hitachi U3300 UV/VIS spectrophotometer. Infrared (IR) spectra were measured on a Jasco FT-IR-5300 Fourier transform infrared spectrometer. The wave numbers reported were referenced to the polystyrene 1601 $cm^{-1}$ absorption. Absorption intensities were recorded by the following abbreviations: s, strong; m, medium; w, weak. The fluorescent intensity was measured on a Hitach F-4500 Florescence Spectrophotometer. Proton NMR spectra were obtained on a Varian Mercury-400 (400 MHz) spectrometer by use of chloroform-d as the solvent and sodium 3-(trimethylsilyl) propionate as internal standard. Carbon-13 NMR spectra were obtained on a Varian Mercury-400 (100 MHz) spectrometer by use of chloroform-d or $D_2O$ as the solvent. Carbon-13 chemical shifts were referenced to the center of the $CDCl_3$ triplet (δ77.0 ppm). Multiplicities are recorded by the following abbreviations: s, singlet; d, doublet; t, triplet; q, quartet; m, multiplet; J, coupling constant (hertz). Hight-resolution mass spectra were obtained by means of a JEOL JMS-HX110 mass spectrometer. Electrospray ionization mass spectrometry (ESI-MS) analyses were performed on a quadrupole ion trap mass analyzer fitted with an electrospray ionization source of Finnigan LCQ, Finnigan MAT.

Computation was performed on a Silicon Graphics O2+ workstation. Software Chemoffice Ultra 10.0 was used to draw chemical structures and synthetic schemes. The software PCModel 7.5 was used for energy minimized with the consistent valence force field (CVFF) until the maximum derivative was less than 1.0 kcal $mol^{-1}$ $Å^{-1}$.

EXAMPLE 1

Synthesis of 1,4-bis-(3,4-methoxyphenyl) butane ($C_{20}H_{26}O_4$, FW=330.42) "Compound A"

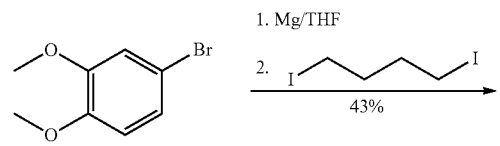

Chemical Formula: $C_8H_9BrO_2$
Molecular Weight: 217.06

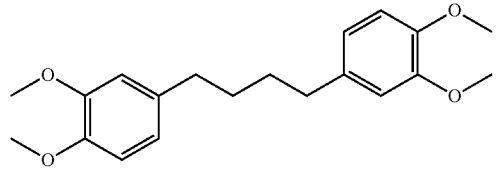

Chemical Formula: $C_{20}H_{26}O_4$
Molecular Weight: 330.42

The compound was synthesized using a modification of Nakamura, et al.[20] involving coupling of 1,4-diiodobutane with Grignard reagent derived from 3,4-dimethoxybromobenzene in 43% yield. m.p. 93-94° C. (literature[21] m.p. 91-92° C.). HPLC purity: 99.25%.

$^1$HNMR ($CDCl_3$, 300 MHz): δ=1.58-1.68 (m, 4H), 2.55-2.65 (m, 4H), 3.85 (s, 6H), 3.86 (s, 6H), 6.69 (s, 2H), 6.70 (dd, J=7.9, 1.6 Hz, 2H), 6.78 (d, J=7.9 Hz, 2H) ppm, consistent with the structure.

$^{13}$CNMR ($CDCl_3$, 75 MHz): δ=31.1, 35.3, 55.7, 55.9, 111.2, 111.7, 120.1, 135.2, 147.0, 148.7 ppm; consistent with the structure.

Analysis: calculated for $C_{20}H_{26}O_4$, C, 72.70; H, 7.95; found C, 72.51; H: 7.82.

MS (EI), m/e=331 (M+1); consistent with $C_{20}H_{26}O_4$

EXAMPLE 2

Synthesis of 1,4-bis-(3,4-hydroxyphenyl) butane (alternatively named 1,4-bis(catechol-4-yl)-butane) [$C_{16}H_{18}O_4$, FW=274.31) "Compound B"

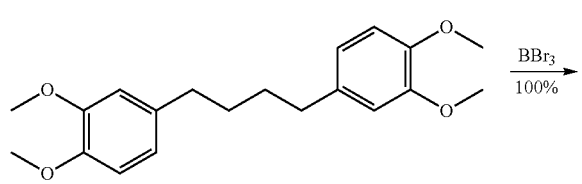

Chemical Formula: $C_{20}H_{26}O_4$
Molecular Weight: 330.42

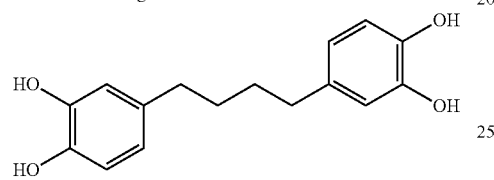

Chemical Formula: $C_{16}H_{18}O_4$
Molecular Weight: 274.31

This compound was synthesized by cleavage of the aromatic methoxy group of the product of Example 1, (1,4-bis-(3,4-methoxyphenyl) butane), using boron tribromide[22] in quantitative yield. The crude product was found to be pure by TLC, so it was used for the preparation of derivatives without further purification. Analytical sample was purified by a flash silica gel chromatographic column using dichloromethane and methanol (95:5, V/V) as eluant.

m.p 140-142° C. HPLC purity: 98.5%.

$^1$H NMR (DMSO-$d_6$, 300 MHz): δ=1.60 (t, J=6.5 Hz, 4H, 2 $CH_2$), 2.65 (t, J=6.5 Hz, 4H, 2 $CH_2$), 6.65-6.85 (m, 6H, 6 Ar—H), 9.56 (brs, 4H, 4OH) ppm; consistent with the structure.

$^{13}$C NMR (DMSO-$d_6$, 75 MHz): δ=31.5, 36.3, 114.5, 115.8, 120.1, 136.5, 143.5, 145.5 ppm, consistent with the structure.

MS (EI), m/e=275 (M+1), consistent with $C_{16}H_{18}O_4$.

Analysis: calculated for $C_{16}H_{18}O_4$, C: 70.06, H: 6.61; found, C: 70.31, H, 6.82.

EXAMPLE 3

Synthesis of 1,4-bis-(3,4-ethoxyphenyl) butane ($C_{24}H_{34}O_4$, FW=386.52) "Compound C"

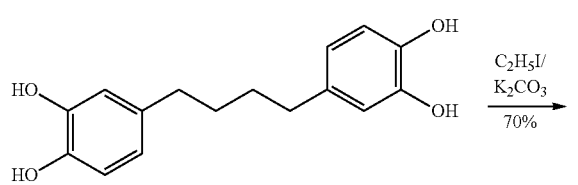

Chemical Formula: $C_{16}H_{18}O_4$
Molecular Weight: 274.31

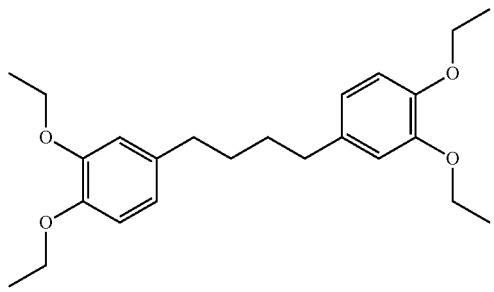

Chemical Formula: $C_{24}H_{34}O_4$
Molecular Weight: 386.52

To a solution of 1,4-bis-(3,4-hydroxyphenyl)butane from Example 2 (700 mg, 2.56 mmol) in acetone (26 mL) was added potassium carbonate (2.39 g, 16.9 mmol, 6.6 equivalents) and iodoethane (2.40 g, 15.4 mmol, 6.0 equivalents) and the mixture heated to reflux for 24 hours. TLC of the reaction indicated completion of the reaction. The reaction mixture was cooled to room temperature, filtered and the solids were washed with acetone. The combined filtrate was concentrated under reduced pressure. The residue was dissolved in ethyl acetate (100 mL) and washed with water (50 mL). The aqueous layer was re-extracted with ethyl acetate (50 mL). The combined organic extracts were dried over anhydrous $Na_2SO_4$ and concentrated under reduced pressure to give the crude product (1.06 g), which was crystallized from ethyl acetate-isopropanol (1:1, 6 mL) to give a pure crystalline product (700 mg, 70% yield).

m.p. 113-115° C. HPLC purity: 98.50%.

$^1$H NMR ($CDCl_3$, 300 MHz): δ=1.43 (t, J=6.8 Hz, 6H), 1.44 (t, J=6.8 Hz, 6H), 1.61-1.65 (m, 4H), 2.40-2.60 (m, 4H), 4.06 (q, J=6.8 Hz, 4H), 4.07 (q, J=6.8 Hz, 4H), 6.63-6.72 (m, 4H), 6.79 (d, J=8.2 Hz, 2H) ppm; consistent with the structure.

$^{13}$C NMR ($CDCl_3$, 75 MHz): δ=14.9, 31.1, 35.3, 64.5, 64.7, 113.9, 114.2, 120.4, 135.5, 146.8, 148.6 ppm; consistent with the structure.

Analysis: calculated for $C_{24}H_{34}O_4$, C: 74.57, H: 8.88; found, C: 74.78, H: 8.75; consistent with the structure.

EXAMPLE 4

Synthesis of 1,4-bis{3,4-bis[3-(piperidin-1-yl) propoxy]phenyl}-butane ($C_{48}H_{78}N_4O_4$, FW=775.16) "Compound D"

This compound could be synthesized by at least two methods.

Method 1: Using Potassium Carbonate as a Catalyst

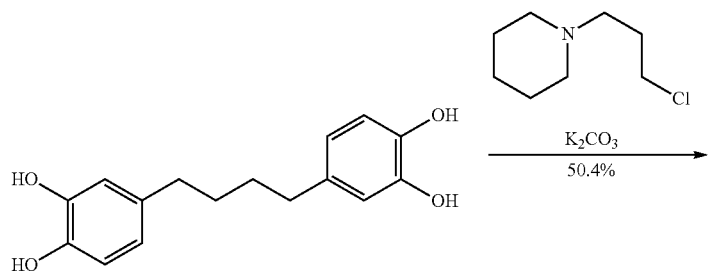

Chemical Formula: $C_{16}H_{18}O_4$
Molecular Weight: 274.31

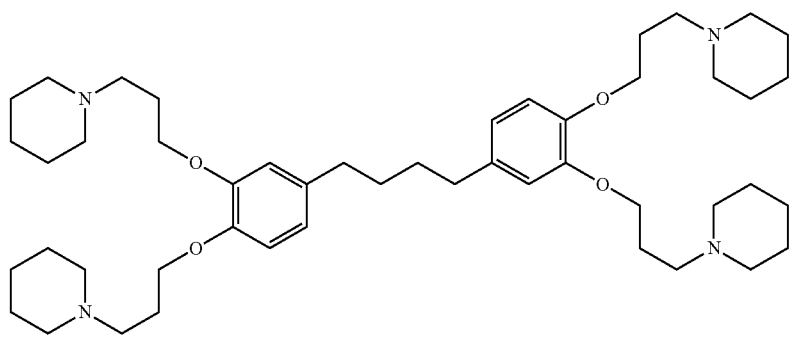

Chemical Formula: $C_{48}H_{78}N_4O_4$
Molecular Weight: 775.16

To a solution of 1,4-bis-(3,4-hydroxyphenyl)butane (1.10 g, 4.0 mmol) in acetone (40 mL) was added potassium carbonate (13.25 g, 96 mmol, 24 equivalents), N-(3 chloropropyl)piperidine hydrochloride (9.5 g, 48 mmol, 12 equivalents) and sodium iodide (2.4 g, 16 mmol, 4 equivalents) and the mixture was heated to reflux for 40 hours. TLC indicated completion of the reaction. The reaction mixture was filtered and the solids were washed with acetone. The combined filtrate was concentrated in vacuo. Hexane (200 mL) was added to the residue and the mixture was heated at 60° C. for 15 mm on a Rotavapor™ device. The hexane layer was decanted and the procedure was repeated two more times on the residue. The combined hexane extracts were concentrated under reduced pressure to give the crude product. It was purified by silica gel column chromatography using silica gel (250 g) and gradient elution with hexane: ethyl acetate: triethylamine (5:5:0.5) to ethyl acetate:methanol: triethylamine (9:1:0.5) to give the pure product (1.56 g, 50.4% yield) as a white solid. It was further purified by crystallization from ethyl acetate-hexane to give a crystalline product (1.03 g).

m.p. 91-93° C. HPLC purity: 99.43%.

$^1$H NMR (CDCl$_3$, 100 MHz): δ=1.38-1.50 (m, 8H), 1.53-1.68 (m, 20H), 1.95-2.07 (m, 8H), 2.35-2.60 (m, 28H), 3.9 (t, J=6.4 Hz, 4H), 4.0 (t, J=6.4 Hz, 4H), 6.63-6.72 (m, 4H), 6.77 (d, J=8.0 Hz, 2H) ppm, consistent with the structure.

$^{13}$C NMR (CDCl$_3$, 75 MHz): δ=24.5, 27.0, 31.3, 35.4, 54.7, 56.2, 67.9, 68.1, 114.4, 114.7, 120.6, 135.7, 147.1, 149.0 ppm, consistent with the structure.

Analysis: calculated for $C_{48}H_{78}N_4O_4$, C: 74.37, H: 10.16, N: 7.23; found, C: 74.07, H: 10.06, N: 7.13.

MS (ESI): m/z=803.7 (M+H)$^+$, 802.7 (M), 678.6, 402.4, 126.0, consistent with the structure.

Method 2: Using Sodium Hydride as a Catalyst

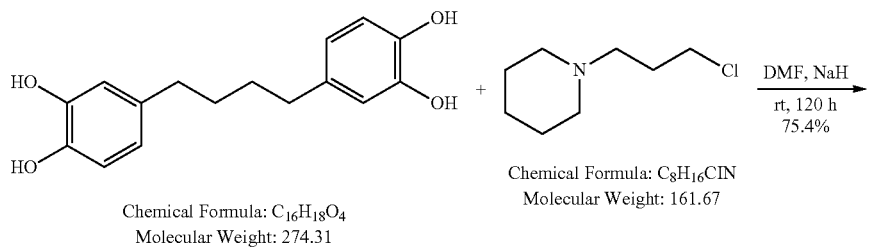

Chemical Formula: $C_{16}H_{18}O_4$
Molecular Weight: 274.31

Chemical Formula: $C_8H_{16}ClN$
Molecular Weight: 161.67

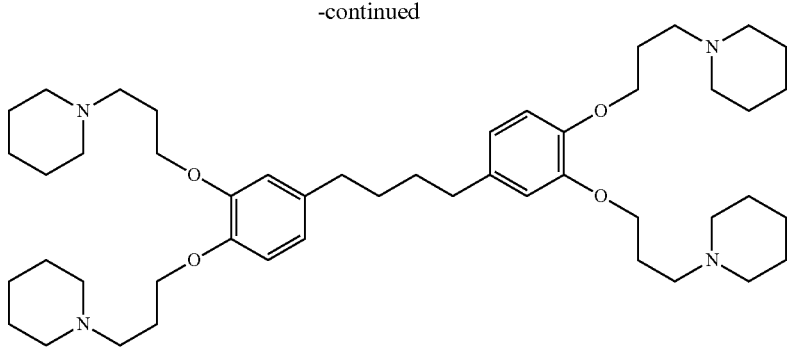

Chemical Formula: $C_{48}H_{78}N_4O_4$
Molecular Weight: 775.16

To a solution of 1,4-bis(3,4-dihydroxyphenyl)-butane (13.0 g, 45.78 mmols) in anhydrous DMF (1 L) was added 60% suspension of sodium hydride in paraffin (9.9 g, 248 mmol 5.4 equivalents) and the mixture was heated at 65° C. for one hour. Then the mixture was cooled to room temperature, N-(3-chloropropyl)piperidine (37.0 g, 229 mmol 5.0 equivalents) and sodium iodide (6.9 g, 46 mmol 1 equivalent) were added and the mixture was allowed to stir at room temperature for 120 hours. TLC indicated complete conversion to the product.

The workup of the reaction was carried out by slow addition of the reaction mixture to water (3 L) and diethyl ether (2.5 L). The aqueous layer was extracted again with diethyl ether (2 L). The combined organic extracts were washed with brine (750 mL), dried over anhydrous sodium sulfate and concentrated under reduced pressure. The crude product was purified by silica gel column chromatography. The column was built using silica gel (500 g) and solvent mixture ethyl acetate:methanol:triethylamine (93:2:5) and eluted with the gradient ethyl acetate:methanol:triethylamine (93:2:5 to 91:4:5) to give the product as white solid (26.7 g, yield 75.4%). This product was crystallized from ethyl acetate: hexane mixture to give crystalline compound (21.4 g).

Analytical data are identical to those obtained from sample prepared by method 1.

EXAMPLE 5

Synthesis of 1,4-bis{3,4-bis[3-(piperidin-1-yl) propoxy]phenyl}-butane tetrakis-hydrochloride salt ($C_{48}H_{78}N_4O_4$.4HCl, FW=921.00) "Compound E"

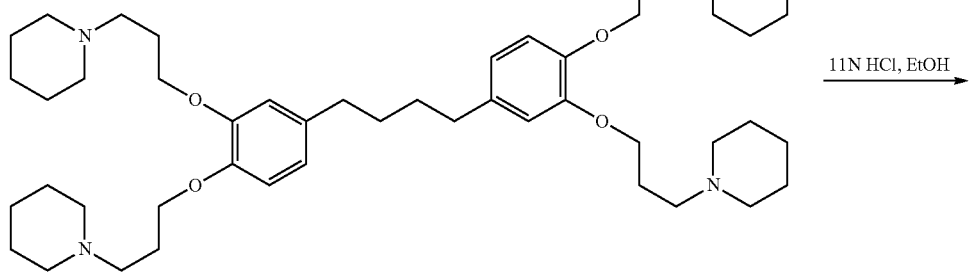

Chemical Formula: $C_{48}H_{78}N_4O_4$
Molecular Weight: 775.16

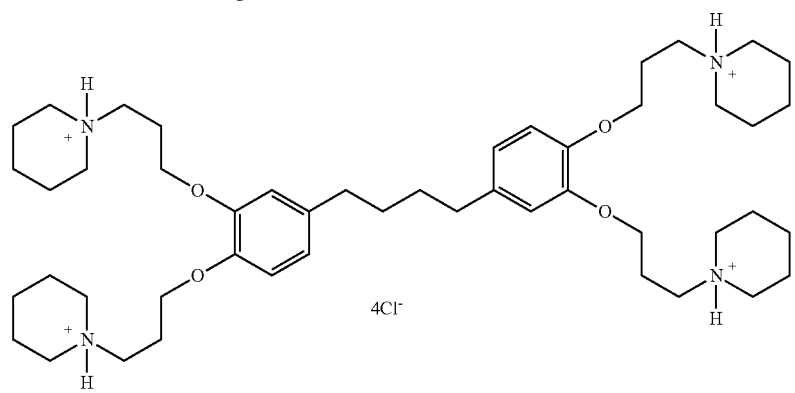

Chemical Formula: $C_{48}H_{82}Cl_4N_4O_4$
Molecular Weight: 921.00

To all ice cooled (0-5° C.) solution of aqueous concentrated HCl (7.0 mL, of 11 N, 77 mmol, 24 equiv.) in 95% ethanol (21 mL) was added dropwise a solution of 1,4-bis{3,4-bis[3-(piperidin-1-yl)propoxy]phenyl}-butane (2.50 g, 3.225 mmol) in 95% ethanol (21 mL)*. The solution was allowed to stir at 0-5° C. for three hours and the solvent was removed on a rotary evaporator keeping the temperature of the water bath at 45° C. The hydrochloride salt was dried under high vacuum for 48 hours. The crude product was then crystallized from ethanol: ether to give 2.46 g of the product (83.2% yield) after drying high vacuum for 72 hours. *Note that the starting material 1,4-bis{3,4-bis[3-(piperidin-1-yl)propoxy]phenyl}-butane did not dissolve completely in 95% ethanol at room temperature, so the mixture was heated at 45° C. during which 1,4-bis{3,4-bis[3-(piperidin-1-yl)propoxy]phenyl}-butane dissolved. The solution was cooled to room temperature and added to the ethanolic HCl solution.

The analytical data for this product are given below.

m.p. 270-280° C. (dec.). HPLC purity: 98.5%. Moisture content by Karl Fisher method: 2.4974%.

Elemental Analysis: $C_{48}H_{82}N_4O_4Cl_4$, required, C: 62.59, H: 8.97, and N: 6.08; found, C: 62.38, H: 9.30; and N: 5.89.

Chlorine elemental analysis by titration method (anhydrous basis): theory, 15.40%; found: 15.44% (100.3% of the theory).

$^1$H NMR (D$_2$O, 300 MHz): δ=1.25-1.50 (m, 8H), 1.55-1.75 (m, 12H), 1.82 (d, J=14.4 Hz, 8H), 2.06-2.10 (m, 8H), 2.39 (s, 4H), 2.76 (t, J=12.1 Hz, 8H), 3.11 (q, J=7.8 Hz, 8H), 3.39 (d, J=11.6 Hz, 8H), 3.98-4.00 (m, 8H), 6.64 (dd, J=1.8, 8.0 Hz, 2H), 6.79 (d, J=1.8 Hz, 2H), 6.84 (d, J=8.0 Hz, 2H) ppm; consistent with the structure.

$^{13}$C NMR (D$_2$O, 100 MHz): δ=24.5, 27.0, 31.3, 35.4, 54.7, 56.2, 67.9, 68.1, 114.4, 114.7, 120.6, 135.7, 147.1, 149.0 ppm; consistent with the structure.

MS (ESI), m/z=777 (M$^+$+2), 775 (M$^+$); consistent with the free base $C_{48}H_{78}N_4O_4$ (775.16).

EXAMPLE 6

Synthesis of 1,4-bis{3,4-bis[2-(1-methyl-piperazin-4-yl)-ethoxy]phenyl}-butane ($C_{44}H_{74}N_8O_4$; FW=779.11) "Compound F"

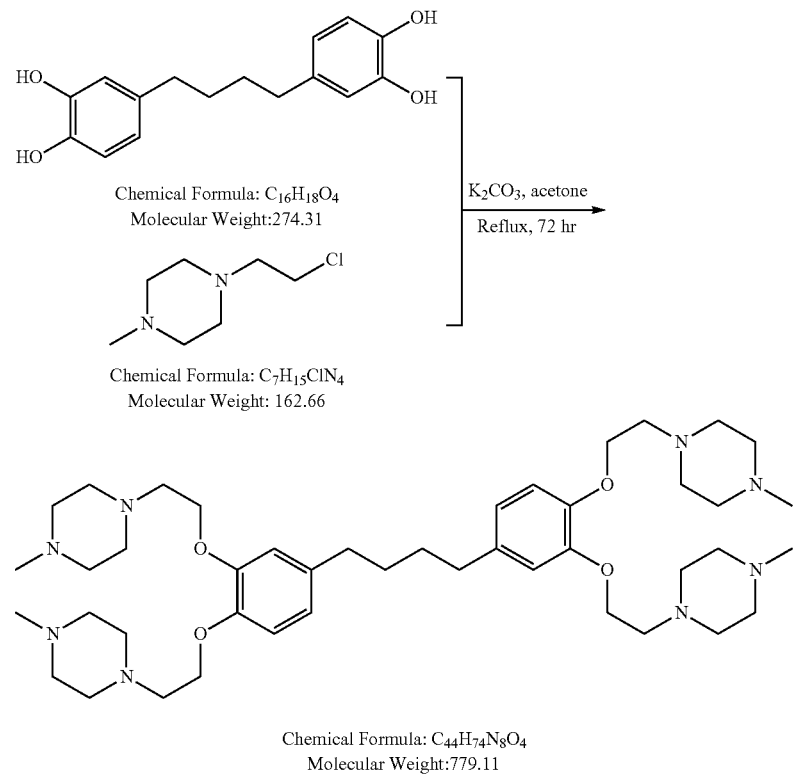

Step 1. Synthesis of N'-methyl-N-2-chloroethylpiperazine from its dihydrochloride salt The N'-methyl-N-2-chloroethylpiperazine dihydrochloride (10.0 g, 45.4 mmol) was added slowly to a mixture of 50% aqueous potassium carbonate (200 mL) and ether (200 mL) and the mixture was stirred for 30 min., layers were separated, aqueous layer extracted with ether (2×200 mL). Combined organic extracts were dried on anhydrous sodium sulfate and concentrated to give N'-methyl-N-2-chloroethylpiperazine (6.2 g).

Step 2: synthesis of 1,4-bis{3,4-bis[2-(1-methyl-piperazin-4-yl)-ethoxy]phenyl}-butane To a solution of compound 2 (1.0 g, 3.65 mmol) in acetone (40 mL) were added anhydrous potassium carbonate (2.52 g, 18.25 mmol, 5 equivalents), and N'-methyl-N-2-chloroethylpiparazine (2.90, 18.25 mmol) were added and the mixture was refluxed. After about 36 hours, additional amounts of potassium carbonate (2.528 g) and N'-methyl-N-2-chloroethylpiparazine (2.90 g) were added and refluxing was continued for 36 more hours. The reaction mixture was cooled to room temperature, filtered, washed with acetone (200 mL) and concentrated. The crude was purified by silica gel (250 g) column chromatography using gradient elution with $CH_2Cl_2$:MeOH:$Et_3$N respectively of 85:10:5 to 65:30:5, to give the title compound (0.88 g, 31.1%). It was further purified by crystallization from ethyl acetate-hexane.

HPLC purity: 99.67%.

$^1$H NMR (CDCl$_3$, 300 MHz): δ=1.55-1.63 (m, 4H), 2.28 (s, 6H), 2.29 (s, 6H), 2.33-2.63 (m, 36H), 2.81 (t, J=6.0 Hz, 4H), 2.82 (t, J=6.0 Hz, 4H), 4.10 (q, J=6.0 Hz, 8H), 6.67 (dd, J=8.2 Hz and 1.7 Hz, 2H), 6.70 (d, J=1.7 Hz, 2H), 6.78 (d, J=8.2 Hz, 2H) ppm; consistent with the structure.

$^{13}$C NMR (CDCl$_3$, 75 MHz): δ=31.2, 35.3, 46.1, 53.7, 55.1, 57.3, 67.3, 67.4, 114.4, 114.7, 120.9, 146.0, 147.9, 148.7 ppm; consistent with the structure.

Analysis: calculated for $C_{44}H_{74}N_8O_4$, C: 67.83, H: 9.59 and N: 14.39; found, C: 67.53, H: 9.71 and N: 14.03.

EXAMPLE 7

Synthesis of 1,4-bis{3,4-bis(2-methyl-thiazol-4-yl-methoxy)phenyl}-butane tetrakis-hydrochloride salt ($C_{36}H_{38}N_4O_4S_4$, FW=718.97) "Compound G"

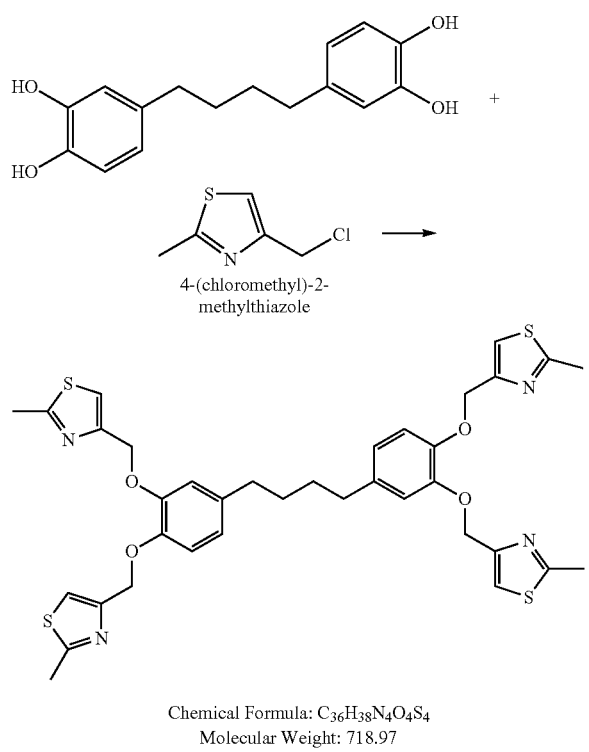

Chemical Formula: $C_{36}H_{38}N_4O_4S_4$
Molecular Weight: 718.97

First, 4-chloromethyl-2-methyl thiazole was generated from its hydrochloride. This was done by adding 4-chloromethyl-2-methyl thiazole hydrochloride (2.5 g, 13.5 mmol) to 50% aqueous potassium carbonate and ether (30 mL each). The mixture was stirred for 15 minutes. The organic layer was separated, dried over anhydrous $K_2CO_3$ and concentrated to give 4-chloromethyl-2-methyl thiazole (2.01 g). This was used in the synthesis of 1,4-bis{3,4-bis(2-methyl-thiazol-4-yl-methoxy)phenyl}-butane tetrakishydrochloride salt as follows.

To an ice cooled solution of 1,4-bis-(3,4-hydroxyphenyl) butane from Example 2 (616 mg, 2.25 mmol) in DMF (15 mL) was added a 60% suspension of sodium hydride in paraffin (54 1 mg, 13.5 mmol, 6 equivalents). The mixture was stirred at 0° C. for 30 minutes and at room temperature for 30 minutes. Then a solution of the 4-chloromethyl-2-methyl thiazole (2.01 g, 13.5 mmol, 6 equivalents) in DMF (5 mL) was added and the reaction mixture was allowed to stir for 16 hours at room temperature. The reaction mixture was added to the saturated aqueous NH$_4$Cl (150 mL) and ether (350 mL). After shaking, the organic layer separated, and the aqueous layer was extracted with ether (150 mL). The combined organic extracts were washed with water (50 mL), brine (50 mL), and dried over anhydrous Na$_2$SO$_4$ and concentrated under reduced pressure to give the crude product. It was purified by silica gel column chromatography using silica gel (250 g) and hexane:ethyl acetate (50:50 to 0:100) as an eluant to give the product as a white solid (0.88 g, 54.3%). It was further purified by crystallization form ethyl acetate-hexane.

m.p. 96-98° C. HPLC purity: 99.99%.

$^1$H NMR (CDCl$_3$) 1.51-1.61 (m, 4H), 2.48-2.60 (m, 4H), 2.71 (s, 6H), 2.72 (s, 6H), 5.20 (s, 4H), 5.22 (s, 4H), 6.69 (dd, J=8.2 Hz, 1.8, 2H), 6.80 (d, J 1.8 Hz, 2H), 6.88 (d, J=8.2 Hz, 2H), 7.18 (s, 4H) ppm; consistent with the structure.

$^{13}$C NMR (CDCl$_3$) 19.1, 30.9, 35.2, 67.8, 68.0, 115.3, 115.4, 115.6, 115.7, 121.5, 136.4, 146.8, 148.5, 152.4, 152.5, 166.1 ppm; consistent with the structure.

Analysis: calculated for $C_{36}H_{38}N_4O_4S_4$, C: 60.13, H: 5.34, and N: 7.79. Found C 60.07, H 5.22, and N: 7.70.

EXAMPLE 8

Synthesis of 1,4-bis{3,4-bis(2-(N,N'-dimethyl-amino)-ethoxy)phenyl}t-butane ($C_{32}H_{54}N_4O_4$, FW=558.41) "Compound H"

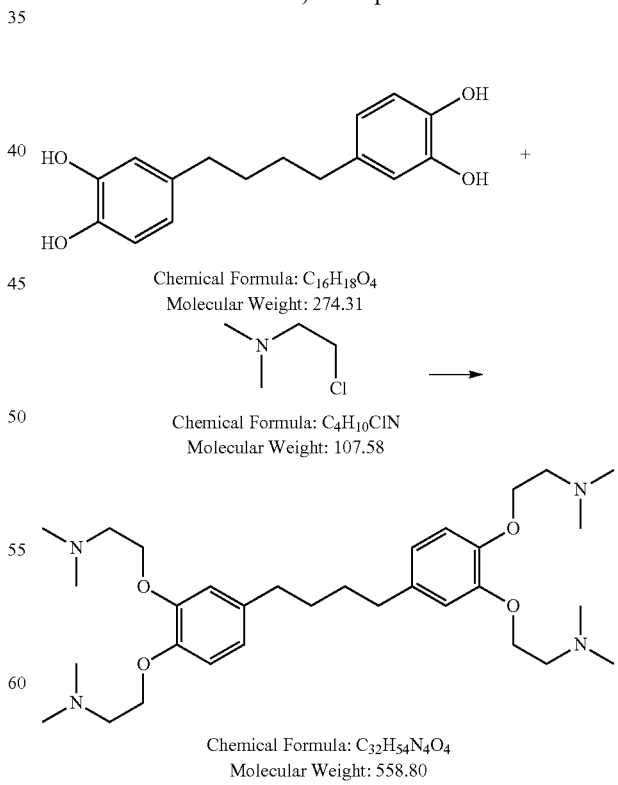

Chemical Formula: $C_{16}H_{18}O_4$
Molecular Weight: 274.31

Chemical Formula: $C_4H_{10}ClN$
Molecular Weight: 107.58

Chemical Formula: $C_{32}H_{54}N_4O_4$
Molecular Weight: 558.80

To a solution of 1,4-bis(3,4-dihydroxyphenyl)-butane (1.096 g, 4 mmol) in acetone (40 mL) were added anhydrous potassium carbonate (6.64 g, 48 mmol) and dimethylaminoethyl chloride hydrochloride (3.46 g, 24 mmol) and the mixture was heated to reflux. After 12 hours an additional amount of potassium carbonate (6.648 g) and dimethylaminoethylchloride hydrochloride (3.46 g) were added and the reaction mixture was heated to reflux for 64 hours. TLC of the reaction mixture indicated completion. The reaction mixture was cooled to room temperature, filtered, washed with acetone (150 mL) and concentrated. The crude obtained was purified by silica gel (250 g) column chromatography using gradient elution $CH_2Cl_2$:MeOH:$Et_3N$ respectively of 94:1:5 to 85:10:5 to give the product (1.28 g, 57.8%). This material was crystallized from ethyl acetatehexane to give further purified product (300 mg).

m. p. 65-67° C. HPLC purity: 99.04%

$^1$H NMR ($CDCl_3$, 300 MHz): δ=1.59-1.63 (m, 4H), 2.33 (s, 12H), 2.34 (s, 12H), 2.50-2.56 (m, 4H), 2.73 (t, J=6.1 Hz, 4H), 2.74 (m, J=6.1 Hz, 4H), 4.07 (q, J=6.1 Hz, 8H), 6.68 (dd, J=7.9 Hz, 1.9 Hz, 2H), 6.7 1 (d, J=1.9 Hz, 2H), 6.80 (d, J=7.9 Hz, 2H) ppm; consistent with the structure.

$^{13}$C NMR ($CDCl_3$, 75 MHz): δ=31.1, 35.3, 45.9, 46.1, 58.3, 67.8, 67.191, 4 0.6, 114.9, 120.9, 136.0, 147.1, 148.9 ppm, consistent with the structure.

Analysis: calculated for $C_{32}H_{54}O_4N_4$, C: 68.78, H: 9.76, and N: 10.03; found, C: 69.82, H: 9.85, and N: 9.83.

As illustrated in the following prophetic Examples A-R, additional chemical reactions can be performed to synthesize compounds according to embodiments of the present invention.

Prophetic Example A

Alternative synthesis of 1,4-bis-3,4-hydroxyphenyl) butane (alternatively named 1,4-bis(catechol-4-yl)-butane)" in Example 2 "Compound B"

Prophetic Example B

Synthesis of 1,4-bis{3,4-bis[2-(piperidin-1-yl) ethoxy]phenyl}-butane-tetrakis-hydrochloride salt; free base ($C_{44}H_{70}N_4O_4$, FW=719.05); 4HCl salt ($C_{44}H_{70}N_4O_4$·4HCl, FW=864.89)

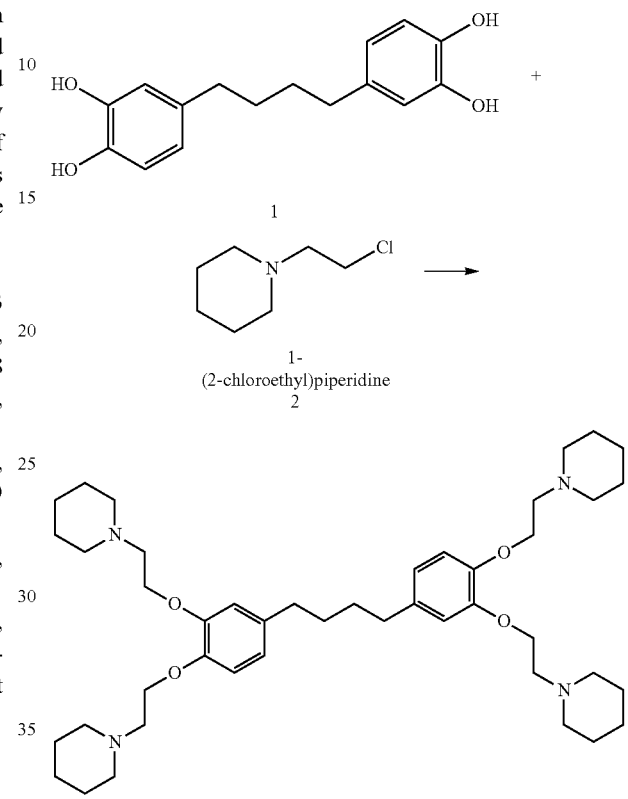

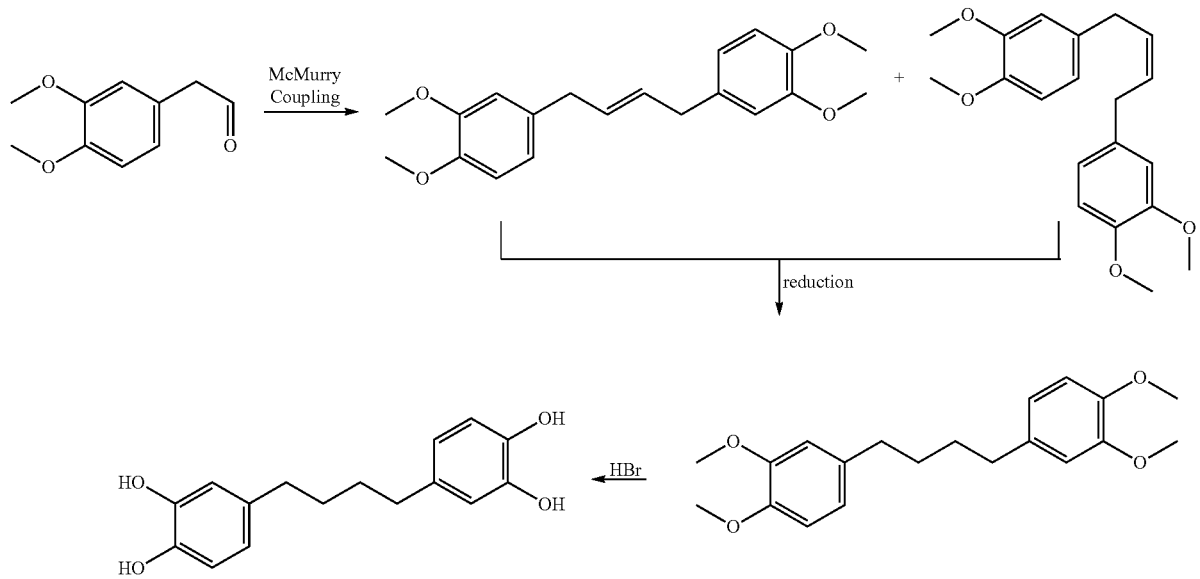

Prophetic Example C

Synthesis of 1,4-bis{3,4-bis[3-(morpholin-1-yl)propoxy]phenyl}-butane tetrakis-hydrochloride salt free base ($C_{44}H_{70}N_4O_8$, FW=783.05); 4HCl salt ($C_{44}H_{70}N_4O_8 \cdot 4HCl$, FW=928.89)

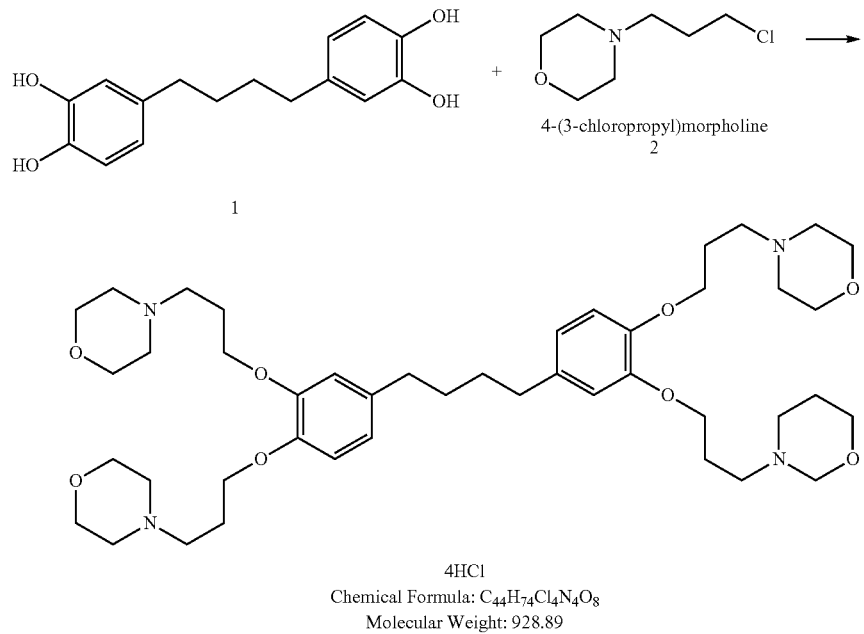

4HCl
Chemical Formula: $C_{44}H_{74}Cl_4N_4O_8$
Molecular Weight: 928.89

Prophetic Example D

Synthesis of 1,4-bis{3,4-bis[2-(morpholin-1-yl)ethoxy]phenyl}-butane tetrakis-hydrochloride salt free base ($C_{40}H_{62}N_4O_8$, FW=726.94); 4HCl salt ($C_{40}H_{62}N_4O_8 \cdot 4HCl$, FW=872.79)

Prophetic Example E

Synthesis of 1,4-bis{3,4-bis[2-(pyrrolidin-1-yl)ethoxy]phenyl}-butane tetrakis-hydrochloride salt free base ($C_{40}H_{62}N_4O_4$, FW=662.94); 4HCl salt ($C_{40}H_{62}N_4O_4 \cdot 4HCl$, FW=808.79)

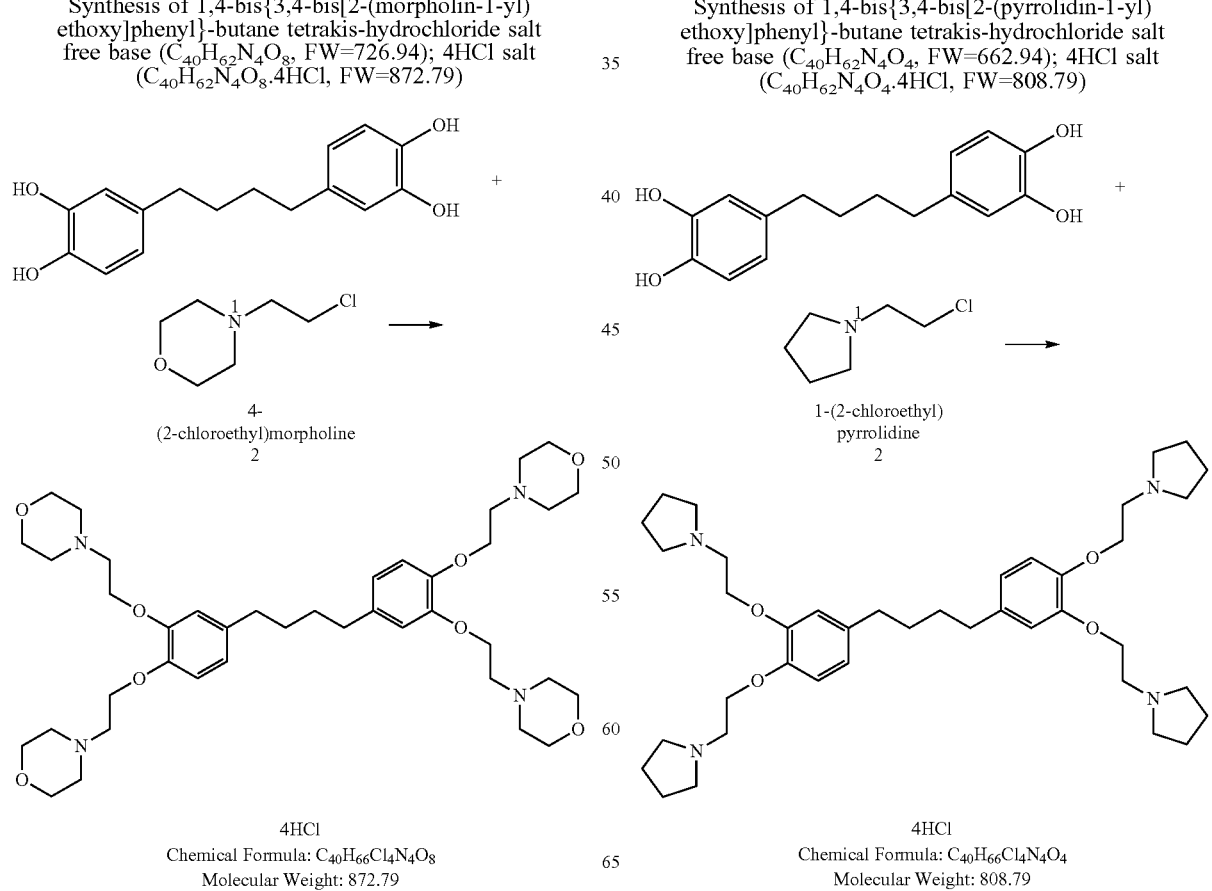

4HCl
Chemical Formula: $C_{40}H_{66}Cl_4N_4O_8$
Molecular Weight: 872.79

4HCl
Chemical Formula: $C_{40}H_{66}Cl_4N_4O_4$
Molecular Weight: 808.79

Prophetic Example F

Synthesis of 1,4-bis{3,4-bis[2-(1-methyl-piperazin-4-yl)-ethoxy]phenyl}-butane tetrakishydrochloride salt free base ($C_{44}H_{74}N_8O_4$; FW=779.11); 4HCl salt: ($C_{44}H_{74}N_8O_4$·4HCl, FW=924.95)

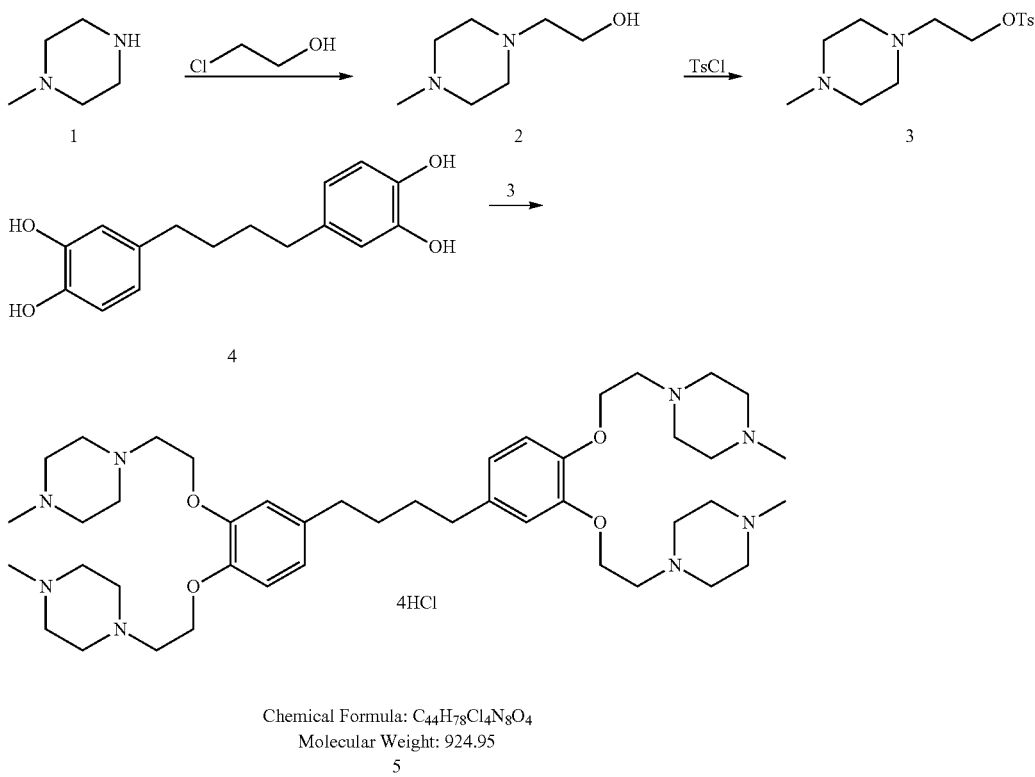

Chemical Formula: $C_{44}H_{78}Cl_4N_8O_4$
Molecular Weight: 924.95

5

Prophetic Example G

Synthesis of 1,4-bis{3,4-bis(2-hydroxyethoxy)phenyl}-butane free base ($C_{24}H_{34}O_8$, FW=450.23)

Method 1

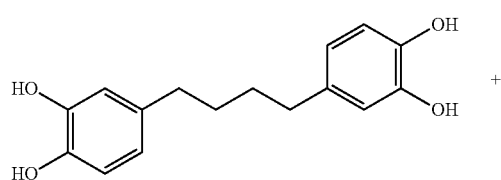

+

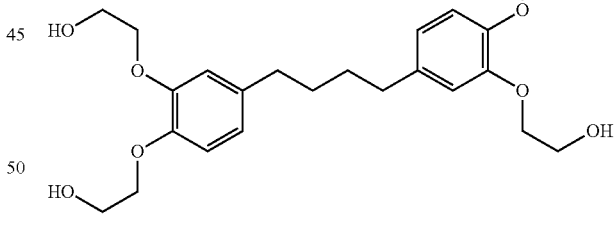

Chemical Formula: $C_{24}H_{34}O_8$
Molecular Weight: 450.52

Method 2

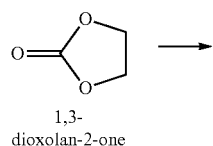

1,3-dioxolan-2-one

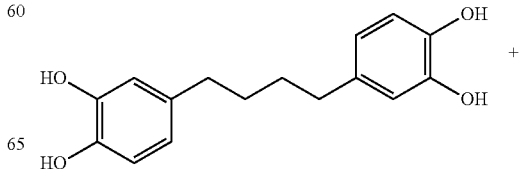

+

43
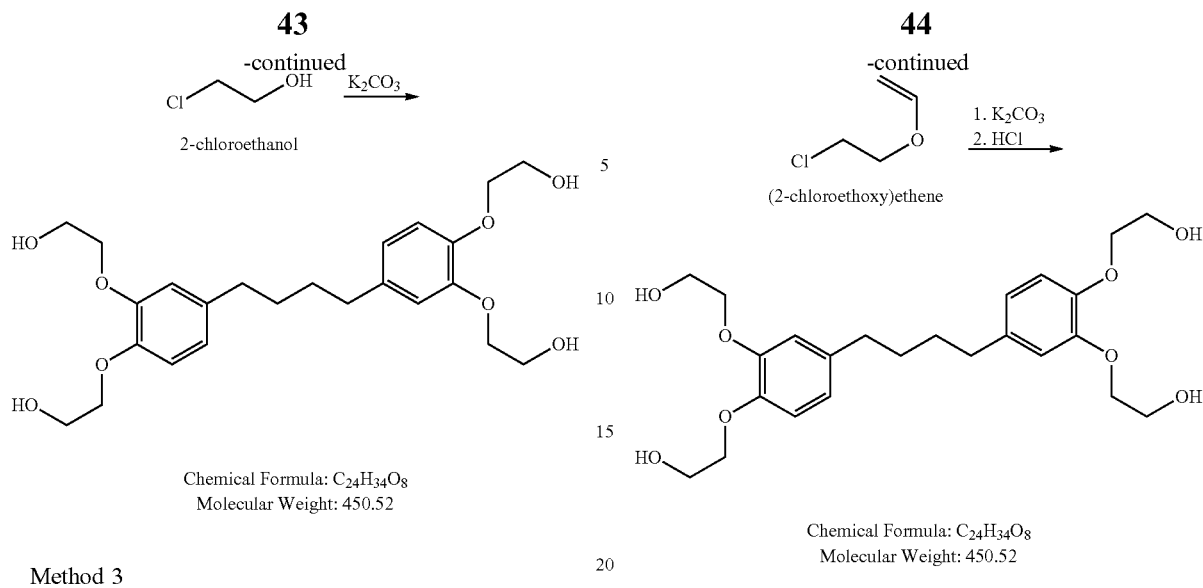
Method 3
44
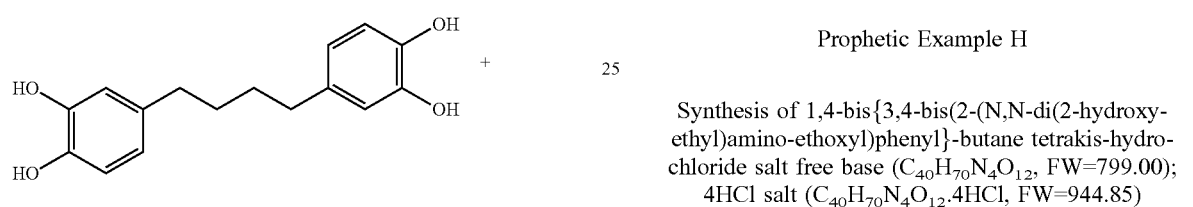
Prophetic Example H
Synthesis of 1,4-bis{3,4-bis(2-(N,N-di(2-hydroxy-ethyl)amino-ethoxyl)phenyl}-butane tetrakis-hydrochloride salt free base ($C_{40}H_{70}N_4O_{12}$, FW=799.00); 4HCl salt ($C_{40}H_{70}N_4O_{12} \cdot 4HCl$, FW=944.85)
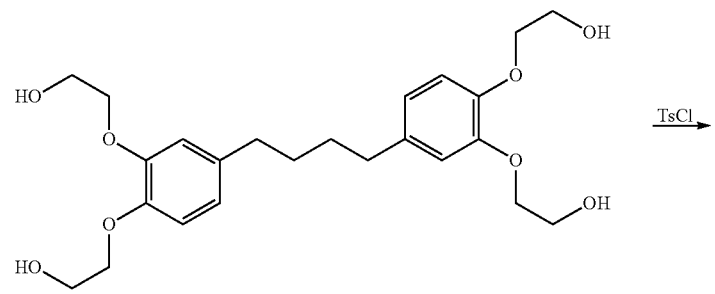
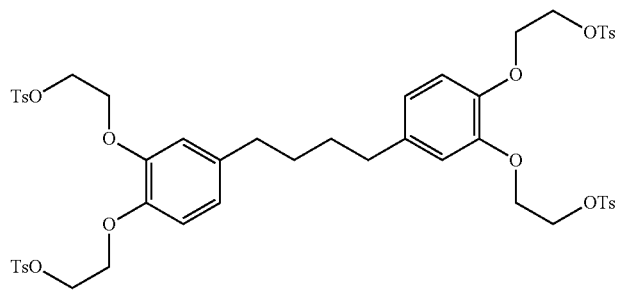

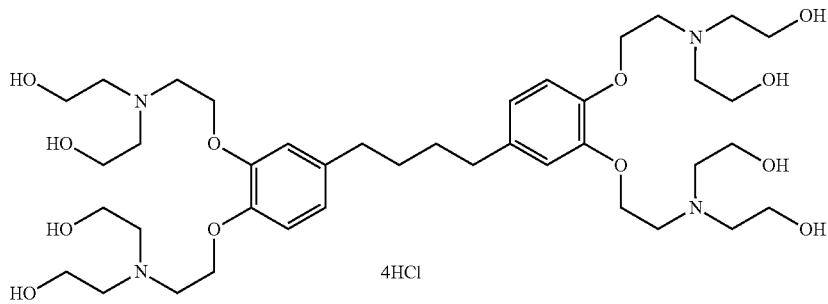
Chemical Formula: $C_{40}H_{74}Cl_4N_4O_{12}$
Molecular Weight: 944.85
Prophetic Example I
Synthesis of 1,4-bis{3,4-bis[2-(2-hydroxyethoxy)ethoxyl]phenyl}-butane free base ($C_{32}H_{50}O_{12}$, FW=626.73)
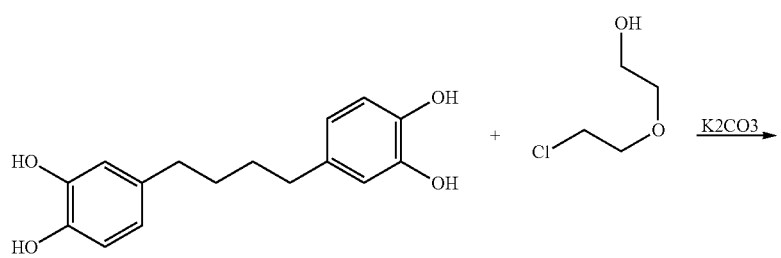
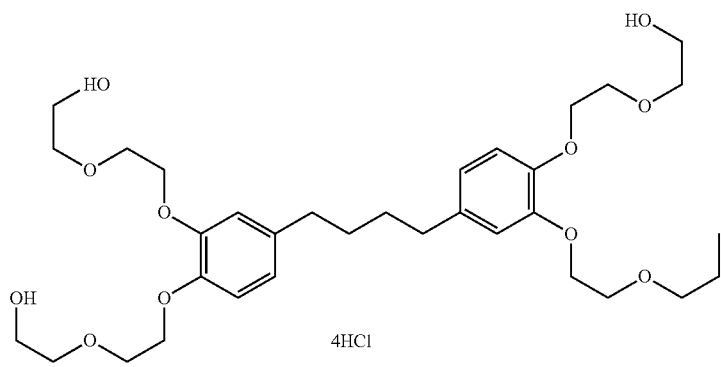
Chemical Formula: $C_{32}H_{50}O_{12}$
Molecular Weight: 626.73

Prophetic Example J
Synthesis of 1,4-bis{3,4-bis[2-(piperidin-1-yl)ethyl-carbamoyloxy]phenyl}-butane tetrakis-hydrochloride salt free base ($C_{48}H_{74}N_8O_8$, FW=890.15), 4HCl salt ($C_{48}H_{74}N_8O_8 \cdot 4HCl$, FW=1036.99)
Method 1
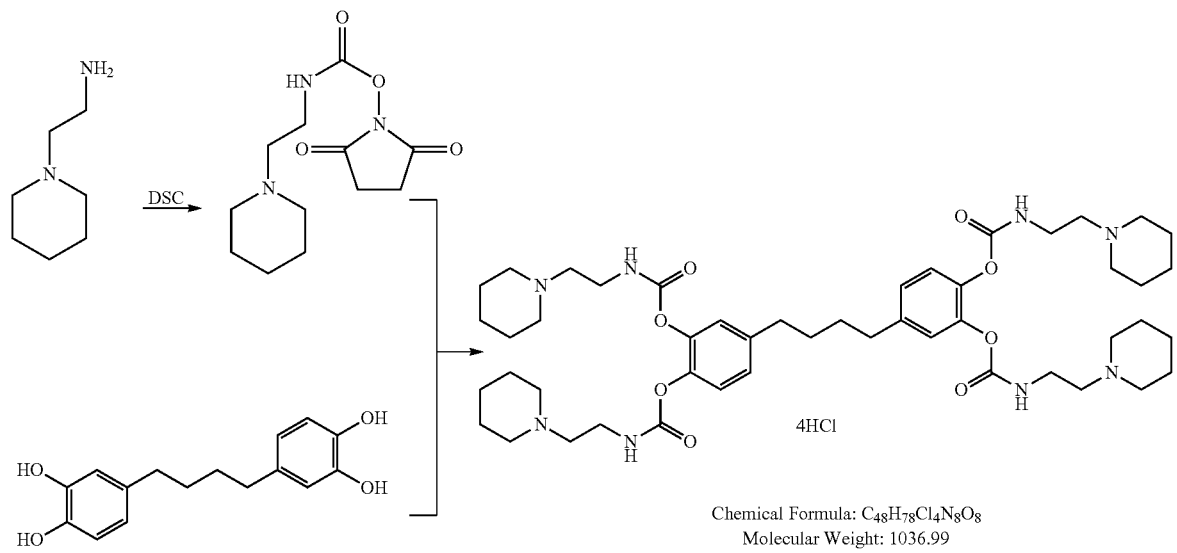
Method 2
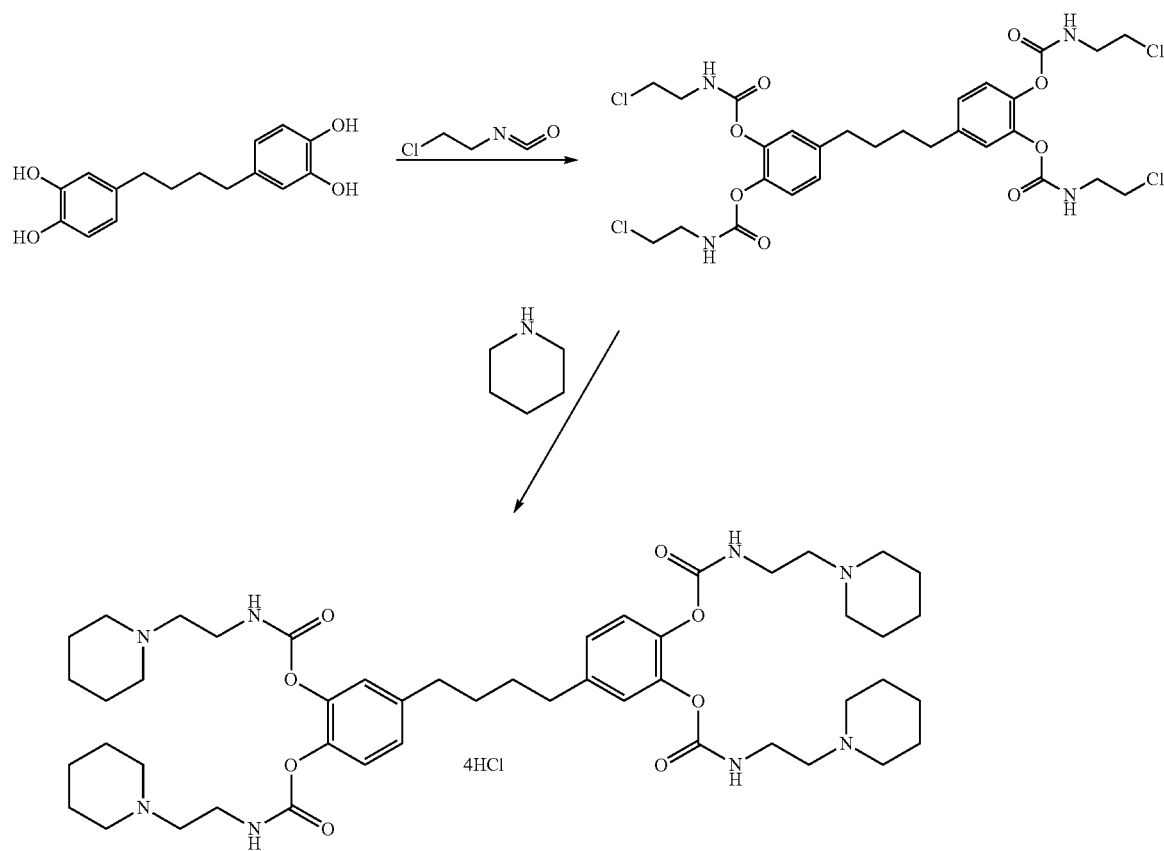

Prophetic Example K

Synthesis of 1,4-bis{3,4-bis[2-(morpholin-1-yl)ethylcarbamoyloxy]phenyl}-butane tetrakis-hydrochloride salt free base ($C_{44}H_{66}N_8O_{12}$, FW=899.04); 4HCl salt ($C_{44}H_{66}N_8O_{12} \cdot 4HCl$, FW=1044.89)

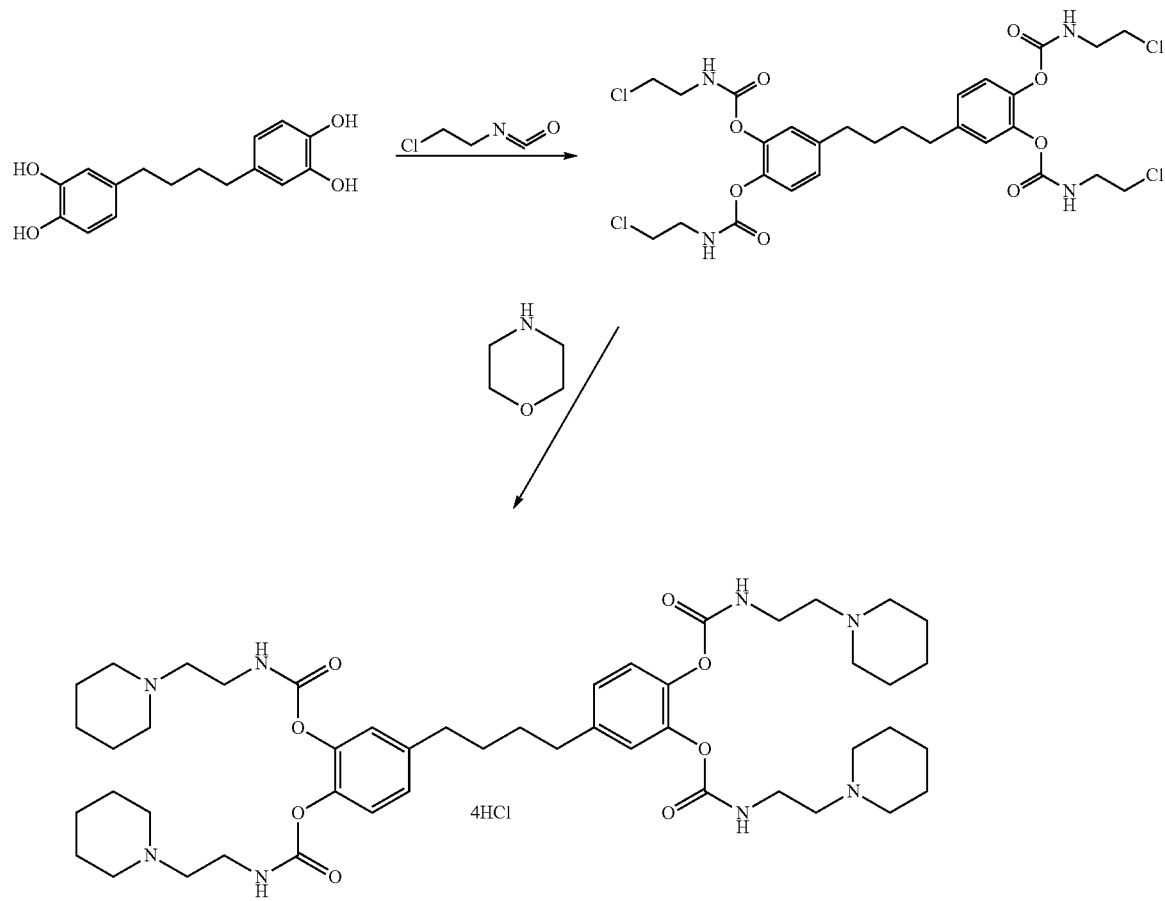 [SMILES: Oc1ccc(CCCCc2ccc(O)c(O)c2)cc1O ; O=C=NCCCl ; O=C(NCCCl)Oc1ccc(CCCCc2ccc(OC(=O)NCCCl)c(OC(=O)NCCCl)c2)cc1OC(=O)NCCCl ; C1CCNCC1 ; O=C(NCCN1CCCCC1)Oc1ccc(CCCCc2ccc(OC(=O)NCCN3CCCCC3)c(OC(=O)NCCN3CCCCC3)c2)cc1OC(=O)NCCN1CCCCC1]

Chemical Formula: $C_{44}H_{70}Cl_4N_8O_{12}$
Molecular Weight: 1044.89

Prophetic Example L

Synthesis of 1,4-bis{3,4-bis[(2-N,N-dimethylaminoethyl)carbamoyloxy]phenyl}-butane free base ($C_{36}H_{58}N_8O_8$, FW=730.89)

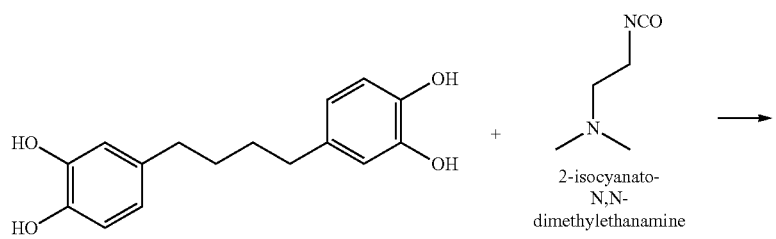

2-isocyanato-N,N-dimethylethanamine

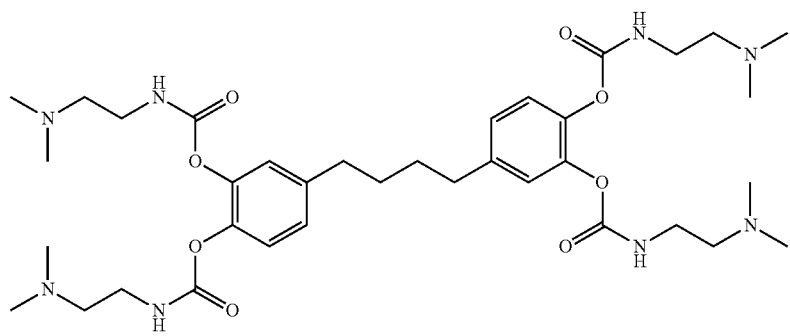
Chemical Formula: $C_{36}H_{58}N_8O_8$
Molecular Weight: 730.89
Prophetic Example M
Synthesis of 1,4-bis{3,4-bis[(furan-2-yl)methyl-carbamoyloxy]phenyl}-butane free base
($C_{40}H_{38}N_4O_{12}$, FW=766.75)
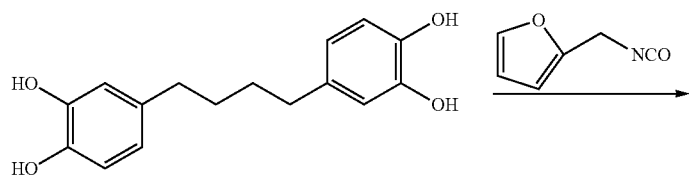
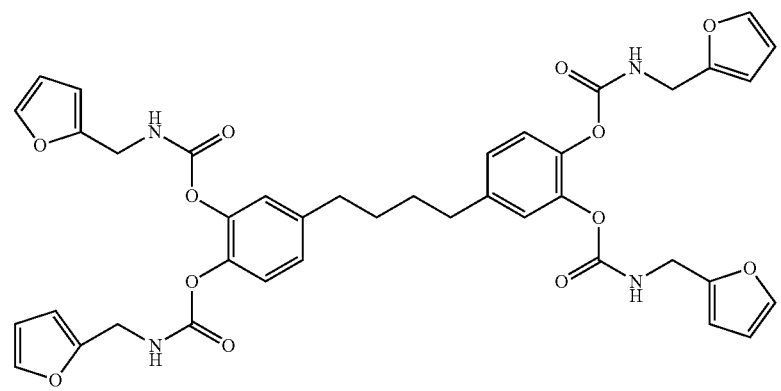
Chemical Formula: $C_{40}H_{38}N_4O_{12}$
Molecular Weight: 766.75

Prophetic Example N

Synthesis of 1,4-bis(3,4-dimethoxyphenyl)-2,3-bis(chloromethyl)-(2S,3R)-butane ($C_{22}H_{28}Cl_2O_4$, FW=427.36)

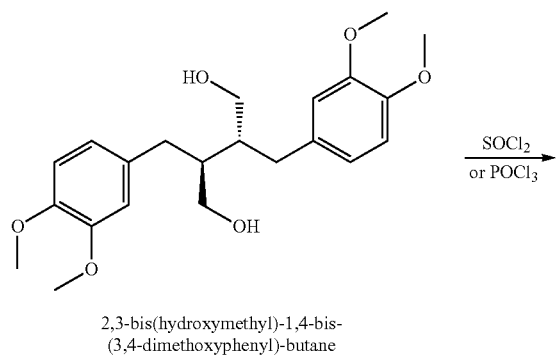

2,3-bis(hydroxymethyl)-1,4-bis-(3,4-dimethoxyphenyl)-butane

→ SOCl₂ or POCl₃

Chemical Formula: $C_{22}H_{28}Cl_2O_4$
Molecular Weight: 427.36

Prophetic Example O

Synthesis of 1,4-bis(3,4-dimethoxyphenyl)-2,3-bis(bromomethyl)-(2S,3R)-butane ($C_{22}H_{28}Br_2O_4$, FW=516.26)

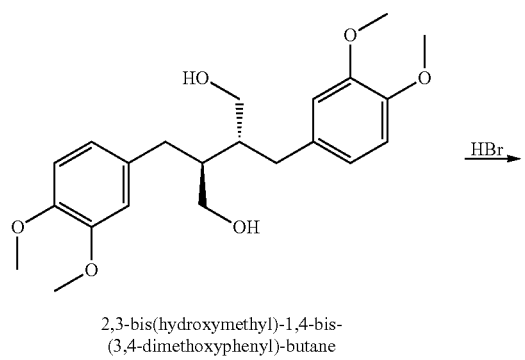

2,3-bis(hydroxymethyl)-1,4-bis-(3,4-dimethoxyphenyl)-butane

→ HBr

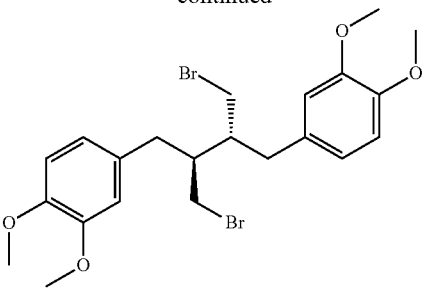

Chemical Formula: $C_{22}H_{28}Br_2O_4$
Molecular Weight: 516.26

Prophetic Example P

Synthesis of 1,4-bis(3,4-dimethoxyphenyl)-2,3-bis(fluoromethyl)-(2S,3R)-butane ($C_{22}H_{28}F_2O_4$, FW=394.45)

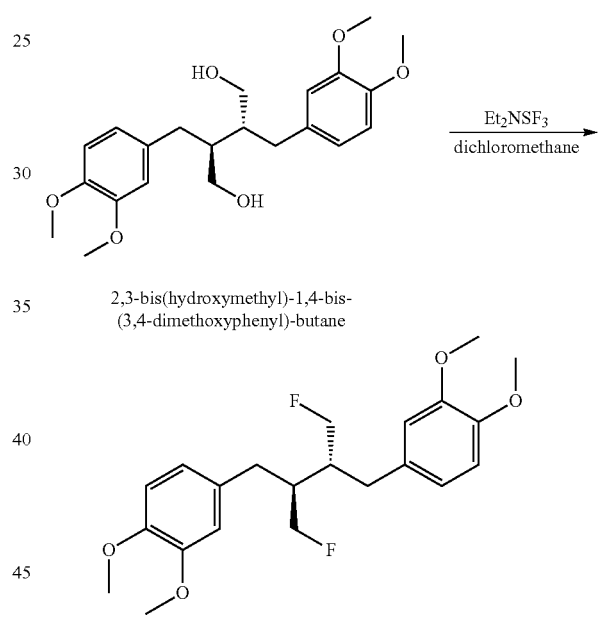

2,3-bis(hydroxymethyl)-1,4-bis-(3,4-dimethoxyphenyl)-butane

→ Et₂NSF₃, dichloromethane

Chemical Formula: $C_{22}H_{28}F_2O_4$
Molecular Weight: 394.45

Prophetic Example Q

Synthesis of 1,4-bis(3,4-dimethoxyphenyl)-2,3-diformyl-(2S,3R)-butane ($C_{22}H_{26}O_6$, FW=386.44)

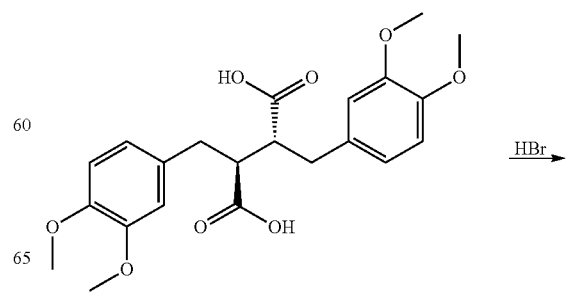

→ HBr

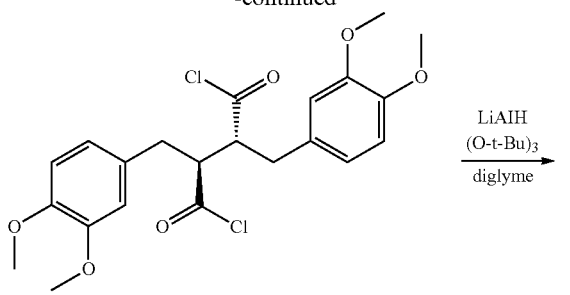

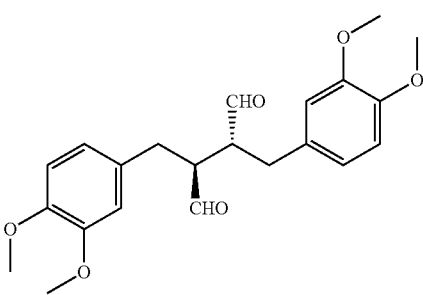

Chemical Formula: C$_{22}$H$_{26}$O$_6$
Molecular Weight: 386.44

Prophetic Example R

Synthesis of 1,4-bis(3,4-dimethoxyphenyl)-2,3-dicyano-(2S,3R)-butane (C$_{22}$H$_{24}$N$_2$O$_4$, FW=380.44)

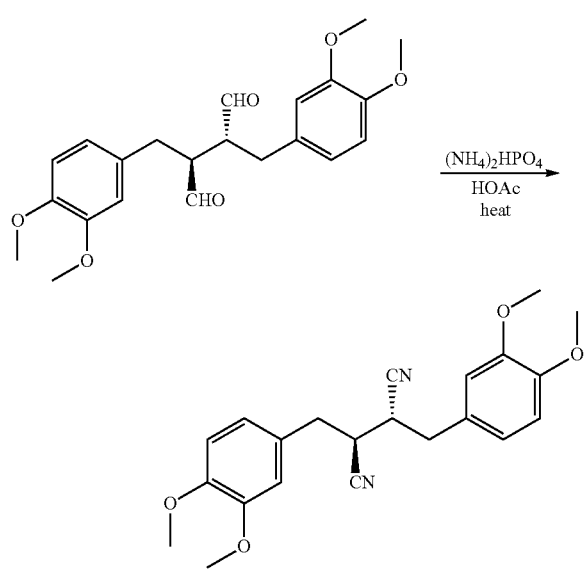

Chemical Formula: C$_{22}$H$_{24}$N$_2$O$_4$
Molecular Weight: 380.44

The invention will further be described with respect to the following specific, non-limiting working examples relating to in vitro cytotoxicity and effectiveness studies, following the general protocols that were performed.

Cytotoxicity and Effectiveness Studies

Certain of the compounds of the present invention have been studied in vitro. The in vitro studies have established that the various classes of the NDGA derivatives of the present invention would be safe and effective for prophylactic or after-onset treatment of a viral infection or a proliferative, inflammatory, metabolic or vascular disease. The following examples explain the studies involved in such testing.

Cytotoxicity Studies

Studies performed regarding cytotoxicity included the well-known MTS, Trypan Blue and MTT protocols. The MTS studies were done using the CellTiter 96®AQ$_{ueous}$ One Solution Cell Proliferation Assay (Promega Corporation, Madison, Wis. USA). Metabolically active, namely viable, cells turn MTS, a tetrazolium compound (3-(4,5-dimethylthiazol-2-yl)-5-(3-carboxymethoxyphenyl)-2-(4-sulfophenyl)-2H-tetrazolium, inner salt) into colored formazan, which is soluble in tissue culture medium. The measurement of the absorbance of the formazan is read at 490 nm. The ready to use reagent is added directly to the cells in media in 96-well plates, incubated 1-4 hours and the results are recorded by the plate reader. The IC$_{50}$ is estimated by graphing the gathered data. The IC$_{50}$ is the concentration of the tested material that inhibits 50% of growth or viability of the tested material compared to a control.

In the Trypan Blue assay, cells are trypsinized and a sample is added to a solution of trypan blue dye and saline. Viable cells are able to keep the dye on the outside of their membrane, damaged or dead cells are not. Viable and non-viable (blue) cells are counted, and the percent viable is calculated. The proliferation rate is calculated using the values from placebo treated cells and compares the viability of treated cells to that of non-treated cells.

The MTT assay is a colorimetric method for determining the number of viable cells. Metabolically active cells turn the MTT reagent, (3-(4,5-dimethylthiazol-2-yl)-2,5-diphenyltetrazolium bromide, into purple-colored formazan crystals that are solubilized in dimethyl sulfoxide (DMSO). The MTT reagent is added to MTT (colorless) media. The media is added to the cells and they are incubated for 4 hours. DMSO is added to the cells and mixed. The colored solutions are then read at 540 nm and corrected at 630 nm. The IC$_{50}$ is estimated by graphing the gathered data.

Antiviral Activity SEAP Assay

Antiviral activity is determined using a SEAP (SEcreted Alkaline Phosphatase) assay, in which cells are co-transfected with SEAP and TAT plasmids. TAT is a transactivator of human immunodeficiency virus (HIV) gene expression and is one of the two or more necessary viral regulatory factors (TAT and REV) for HIV gene expression. TAT acts by binding to the TAR RNA element and activating transcription from the long terminal repeat (LTR) promoter. The TAT protein stabilizes elongation of transcription and has also been shown to be involved in transcription initiation. Previous studies have shown that TAT mediates reduction of antibody-dependent T cell proliferation, contributing substantially to the failure of the immune response. TAT also directly stimulates Kaposi's cell growth.

Since TAT has no apparent cellular homologs, this strong positive regulator has become an attractive target for the development of anti-AIDS drugs. In contrast to currently available HIV reverse transcriptase inhibitors (AZT, DDI) or potential protease inhibitors that prevent new rounds of infection, an inhibitor which suppresses viral gene TAT regulated expression of integrated proviral DNA will arrest the virus at an early stage (Hsu et al., *Science* 254:1799-

1802, 1991). Efforts aimed at the elucidation of factors which control gene expression at transcriptional and post-transcriptional levels in host eukaryotes have recently made possible quantitative assessment of TAT function (Sim, *Ann. N.Y. Acad. Sci.* 616: 64-70, 1990). To screen for inhibitors for TAT regulated transactivation (TAT-TRS), the SEAP reporter gene is put under the control of HIV-1 LTR promoter in the plasmid pBC12/HIV/SEAP. The TAT-coded activity is supplied by a second plasmid construct pBC12/CMV/t2. Transient co-transfection of COS-7 cells with these two plasmids leads to secretion of alkaline phosphatase into the culture medium which is analyzed by a simple colorimetric assay (Berger et al., *Gene* 66: 1-10, 1988). The SEAP assay, therefore, provides an indirect determination of TAT transactivation.

In the SEAP assay, an inhibitor should cause reduction of SEAP reporter gene expression via transactivation of the HIV-1 LTR promoter by TAT protein (TAT-TRS). The TAT protein is expressed under the control of a cytomegalovirus promoter and induces the expression of the non-endogenous, heat resistant form of secreted alkaline phosphatase. If TAT transactivation is blocked by a drug, the reporter SEAP will not be excreted into the media. SEAP is detected colorimetrically by the para-nitrophenyl phosphate substrate at 405 nm. See Gnabre[13]. The cells are analyzed by the MTT assay to compare cytotoxicity to SEAP inhibition. The goal is for the drug to inhibit SEAP without being too toxic.

Antiprolifeative Activity

Antiproliferative activity is determined using the TiterT-ACS® Apoptosis Detection Kit (R&D Systems Inc., Minneapolis, Minn. USA) relating to apoptosis of cells based on DNA fragmentation, and by the ELISA VEGF (vascular epithelial growth factor) and survivin assays.

In the DNA fragmentation assay, in situ detection of apoptosis is specifically achieved with TiterTACS® 96-well Apoptosis Detection kit, Catalog No. TA600) (R&D Systems, Inc.), The TiterTACS® assay provides quantification of apoptosis in cultured cells without direct counting of labeled cells using colorimetric detection. Cells are treated with the test compounds, left untreated as experimental negative controls, or treated with TACS nuclease as positive controls. TACS nuclease allows positive controls to be generated for each experimental system: a brief treatment of cells with the TACS nuclease prior to labeling generates DNA breaks in every cell, providing an appropriate positive control specific for the system under study. The TdT enzyme that catalyzes the addition of dNTPs to DNA fragments allows for colorimetric detection of at 450 nm by using a streptavidin-HRP solution followed by the TACS-Sapphire substrate. A high absorbance at 450 nm is indicative of apoptosis in the cells. Treated cells are compared to untreated cells and to nuclease-cleaved cells to assess the extent of apoptosis.

ELISA (Enzyme-Linked ImmunoSorbent Assay) VEGF studies were done following manufacturer's instructions using the Endogen® Human VEGF ELISA kit, Catalog No. EHVEGF (Pierce Biotechnology, Inc., Rockford, Ill. USA). Hypoxic conditions are created for the cells by treating them with desferrioxamine (DFO), which chelates iron and causes the cells to secrete VEGF into the media. The supernatant (media) was removed and frozen for testing, and the cells were counted with the Trypan Blue assay so that the results can be normalized to cell count. The VEGF is measured with a sandwich ELISA that captures the protein in media on an antibody-coated microplate, and then uses a biotinylated antibody reagent to detect the protein. Results from a standard curve enable the user to quantify the amount of protein in each sample.

ELISA-Survivin Assay

Survivin is an inhibitor of apoptosis that is abundantly expressed in many human cancers, but not in normal adult human tissue, and is considered a possible modulator of the terminal effector phase of cell death/survival. Survivin is expressed in $G_2$-M in a cell cycle-dependent manner, binding directly to mitotic spindle microtubules. It appears that survivin phosphorylation on Thr34 may be required to maintain cell viability at cell division, and expression of a phosphorylation-defective survivin mutant has been shown to trigger apoptosis in several human melanoma cell lines. Phosphorylated survivin acts on the caspase pathway to suppress the formation of caspase-3 and caspase-9, thereby inhibiting apoptosis. Thus, compounds that reduce the expression of survivin will be expected to increase the rate of apoptosis and cell death.

Effects of the tested compounds on survivin were studied following manufacturer's instructions using the Surveyor™ IC Human Total Survivin Immunoassay, Catalog No. SUV647 (R&D Systems, Inc.). Cell lysates were analyzed for survivin protein content. The kit includes a plate coated with an antibody specific for survivin and a biotinylated antibody reagent that recognizes survivin bound to the plate. The plate is read on a plate reader set at 450 nm and corrected at 540 nm. A protein assay according to the Bradford method (Bradford, M. 1976, *Anal Biochem* 72: 248-254) was used to quantify and normalize the samples according to total protein content. Results from a standard curve enable the user to quantify the amount of survivin protein in each sample.

Anti-Inflammatory Activity

Anti-inflammatory activity was determined based on the effect of tested compounds on primary human keratinocytes (PHKs). PHKs play an important role in inflammatory processes, synthesizing a number of cytokines, adhesion molecules and growth factors. Studies were conducted to determine whether tested compounds could inhibit keratinocytes to prevent or reduce production of interferon gamma (IFN-γ), interleukin-8 (IL-8), tumor necrosis factor alpha (TNF-α), granulocyte/macrophage colony-stimulating factor (GM-CSF), intercellular adhesion molecule—1 (ICAM-1, also known as CD54) and monocyte chemotactic protein-1 (MCP-1). PHKs are first treated with TNF-α to induce a pro-inflammatory state and release of pro-inflammatory cytokines. Specific cytokines are then assayed following manufacturer's instructions using R&D Systems, Inc.'s protein assays (Quantikine ELISA kits; Catalog Nos. DCP00 for MCP-1 kit, DGM00 for GM-CSF kit, and DIF50 for IFN-γ).

General Protocols for Cytotoxicity Studies Relating to Antiviral and Antiproliferative Activity Three cell lines obtained from ATCC and maintained as directed by ATCC were tested: HeLa (cervical adenocarcinoma), A549 (lung carcinoma), and COS-7 (SV40 transformed monkey kidney). Studies of these cell lines are considered to be indicative of the effect of tested substances on mammalian, including human, diseases.

All compounds were dissolved in DMSO and DMSO is used as the placebo. The samples were first dissolved into 10 mM dilutions in DMSO and then diluted further to 5, 1, 0.5, 0.1, 0.05, and 0.01 mM solutions. These solutions were added to the media at a 1% concentration (1 µl to 100 µl media) to treat the cells with 100, 50, 10, 5, 1, 0.5, and 0.1 µM of the compound. The compounds that were found to have low $IC_{50}$s were diluted further in DMSO. Solutions were checked before use for precipitation, especially the 10 mM solutions. If there was precipitation, they were warmed 65° C. and added to warmed media.

Wells on a 96-well plate were seeded with $1.5\text{-}8\times10^4$ cells in 100 µl media and incubated overnight. The outside wells of the plate were filled with 200 µl sterile, deionized (DI) water to curb media evaporation. After 24 hours, test chemicals were prepared in media at a concentration of 1% media volume. The test sample media were added, mixing with the pipette before adding 100 µl per well. Media was added to the "Media Only" wells. The well plate and its contents were incubated for 24-72 hours, depending on the study conducted. On the day of the MTS assay, the MTS reagent was removed from the refrigerator and brought to room temperature. Using the multichannel pipette, 20 µl of the MTS reagent was added to each well and incubated for one to four hours. The plate was read at 490 nm with a reference wavelength of 690 nm after one hour in the incubator thereafter until the blank wells were at about 0.2 OD. The results were then scanned into a Microsoft® Excel® template designed to perform all necessary calculations when data are entered. The data were checked for statistical errors; data points that are within 10% of the mean of the data points for that group were included. The average of the blanks ("Media Only") were subtracted and the data were inserted into a chart that represents growth response, treated/untreated.

SEAP Protocol

The following SEAP protocol was used as a reporter system for measuring the activity of TAT-mediated transactivation of HIV transcription. The MTT assay measures cellular proliferation and is used to verify that the levels of SEAP activity are not solely due to cytotoxicity. These assays was used in screening for potential drug compound leads as antiviral agents, and particularly, anti-HIV candidates.

COS-7 (green monkey kidney) cells were co-transfected using Fugene 6 reagent (Roche Applied Science, Cat. No. 11815091001, Indianapolis, Ind., USA) with two plasmids: pHIVSEAP (SEAP expression vector under the control of the HIV LTR promoter) and pCTAT (HIV TAT transcription factor expression vector under the control of a CMV (cytomegalovirus) promoter). After test compound treatment for 48 hours, samples were analyzed for SEAP activity at 405 nm after addition of the p-nitrophenyl phosphate substrate. The percentage of SEAP activity inhibition was calculated in relation to the placebo control.

EXAMPLE 9

SEAP/MTT and MTS Studies—Cytotoxicity and Antiviral Effectiveness

The results of the SEAP/MTT and MTS studies on the indicated compounds from the working Examples above based on the general protocols set forth above are set forth in the following Table 3, where the left hand column identifies the compound tested and $EC_{50}$ indicates the concentration of the compound having 50% of the effect of the control. $IC_{50}$ was defined above.

TABLE 3

| Compound | SEAP $EC_{50}$ | COS-7 $IC_{50}$ | A549 $IC_{50}$ | HeLa $IC_{50}$ |
|---|---|---|---|---|
| A | >100 µM | >100 µM | >100 µM | >100 µM |
| C | >100 µM | >100 µM | >100 µM | >100 µM |
| D | 0.7-0.8 µM | 0.8-0.9 µM | 1-2 µM | 5-6 µM |
| E | | | 9 µM | 5-10 µM |
| F | | | >100 µM | >100 µM |
| G | | | >100 µM | >100 µM |
| H | 30-40 µM | 20-30 µM | 20-40 µM | 20-30 µM |

Results from compounds with biological activity in two cell lines tested using the MTS assay as an indicator of cell viability are shown in Table 3. $IC_{50}$ concentrations show various degrees of inhibition of cell viability by these compounds. All compounds were able to reduce cell viability, and therefore, induce apoptosis, in a dose dependent manner. Compound D showed the strongest cell viability inhibition in A549 and HeLa cells, while its hydrochloride salt (Compound E) showed the second strongest inhibition in these two cell lines.

The extent of inhibition of TAT-transactivation as determined by SEAP assay also varied among compounds, as also shown in Table 3. Compound D also showed significant anti-viral activity with $EC_{50}$ around 0.7-0.8 µM. Inhibitory concentrations of cell viability in the test cells (COS-7) as determined by MTT were usually similar as the effective concentrations for TAT-transactivation.

EXAMPLE 10

Antiproliferative Activity Based on TiterTACS®, VEGA and Survivin Aptoptosis Studies The results of the TiterTACS® DNA fragmentation, ELISA VEGA and ELISA survivin apoptosis studies on the indicated compounds from the working Examples above, based on the general protocols above, are set forth in the following Table 4.

TABLE 4

| Compound | DNA fragmentation | Survivin $IC_{50}$ | VEGF $IC_{50}$ |
|---|---|---|---|
| D | Positive | | 4 µM |
| H | Positive | 25 µM | >60 µM |

Positive = induces apoptosis
Negative = does not induce apoptosis

The compounds tested have shown significant reduction of survivin protein levels at low micromolar concentrations. Consequently, they have also shown strong apoptosis induction as determined by the DNA fragmentation assay. Compound H reduces survivin protein expression and is therefore able to induce apoptosis. Compound D is also an inducer of apoptosis. These compounds are able to decrease survivin and induce apoptosis in a dose-dependent manner. Compound H was the most potent inhibitor of survivin protein production with $IC_{50}$ for survivin production around 25 µM.

Release of VEGF protein is also decreased by these compounds. Inhibition of VEGF protein production ranged in the low micromolar concentrations for compound D Inhibition by all compounds was observed in a dose-dependent fashion. Compound D showed an $IC_{50}$ for VEGF production around 4 µM, while compound H showed VEGF $IC_{50}$ at higher than 60 µM.

The results from Table 4 indicate that the compounds of the present invention are effective in inhibiting viral activity and causing cell death (apoptosis) in the cell lines tested. Of the compounds tested, Compounds D, E, and H appear to be more effective than the others due to their lower $EC_{50}$ and $IC_{50}$ values. Compound D appears to be the most effective.

EXAMPLE 11

U.S. National Cancer Institute DTP Human Tumor Cell Line Screen

The United States National Cancer Institute (NCI) provides a developmental therapeutics program (DTP) (http://dtp.nci.nih.gov/branches/btb/ivclsp.html) to screen submitted substances in support of cancer drug discovery. The In Vitro Cell Line Screening Project (IVCLSP) is a dedicated service providing direct support to the DTP anticancer drug discovery program and is designed to screen up to 3,000 compounds per year for potential anticancer activity. The operation of this screen utilizes 60 different human tumor cell lines, representing leukemia, melanoma and cancers of the lung, colon, brain, ovary, breast, prostate, and kidney. The aim is to prioritize for further evaluation, synthetic compounds or natural product samples showing selective growth inhibition or cell killing of particular tumor cell lines. This screen is unique in that the complexity of a 60 cell line dose response produced by a given compound results in a biological response pattern which can be utilized in pattern recognition algorithms (COMPARE program. See: http://dtp.nci.nih.gov/docs/compare/compare.html). Using these algorithms, it is possible to assign a putative mechanism of action to a test compound, or to determine that the response pattern is unique and not similar to that of any of the standard prototype compounds included in the NCI database. In addition, following characterization of various cellular molecular targets in the 60 cell lines, it may be possible to select compounds most likely to interact with a specific molecular target.

The screening is a two-stage process, beginning with the evaluation of all compounds against the 60 cell lines at a single dose of 10 µM. The output from the single dose screen is reported as a mean graph and is available for analysis by the COMPARE program. Compounds which exhibit significant growth inhibition are evaluated against the 60 cell panel at five concentration levels.

Methodology of the In Vitro Cancer Screen

The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 µL at plating densities ranging from 5,000 to 40,000 cells/well depending on the doubling time of individual cell lines. After cell inoculation, the microtiter plates are incubated at 37° C., 5% $CO_2$, 95% air and 100% relative humidity for 24 hours prior to addition of experimental drugs.

After 24 hours, two plates of each cell line are fixed in situ with trichloroacetic acid (TCA), to represent a measurement of the cell population for each cell line at the time of drug addition (Tz). Experimental drugs are solubilized in DMSO at 400-fold the desired final maximum test concentration and stored frozen prior to use. At the time of drug addition, an aliquot of frozen concentrate is thawed and diluted to twice the desired final maximum test concentration with complete medium containing 50 µg/ml gentamicin. Additional four, 10-fold or ½ log serial dilutions are made to provide a total of five drug concentrations plus control. Aliquots of 100 µl of these different drug dilutions are added to the appropriate microtiter wells already containing 100 µl of medium, resulting in the required final drug concentrations.

Following drug addition, the plates are incubated for an additional 48 hours at 37° C., 5% $CO_2$, 95% air, and 100% relative humidity. For adherent cells, the assay is terminated by the addition of cold TCA. Cells are fixed in situ by the gentle addition of 50 µl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 µl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 µl of 80% TCA (final concentration, 16% TCA). Using the seven absorbance measurements [time zero, (Tz), control growth, (C), and test growth in the presence of drug at the five concentration levels (Ti)], the percentage growth is calculated at each of the drug concentrations levels. Percentage growth inhibition is calculated as:

$[(Ti-Tz)/(C-Tz)] \times 100$ for concentrations for which $Ti >/= Tz$ $[(Ti-Tz)/Tz] \times 100$ for concentrations for which $Ti < Tz$.

Three dose response parameters are calculated for each experimental agent. Growth inhibition of 50% ($GI_{50}$) is calculated from $[(Ti-Tz)/(C-Tz)] \times 100 = 50$, which is the drug concentration resulting in a 50% reduction in the net protein increase (as measured by SRB staining) in control cells during the drug incubation. The drug concentration resulting in total growth inhibition (TGI) is calculated from Ti=Tz. The $LC_{50}$ (concentration of drug resulting in a 50% reduction in the measured protein at the end of the drug treatment as compared to that at the beginning) indicating a net loss of cells following treatment is calculated from $[(Ti-Tz)/Tz] \times 100 = -50$. Values are calculated for each of these three parameters if the level of activity is reached; however, if the effect is not reached or is exceeded, the value for that parameter is expressed as greater or less than the maximum or minimum concentration tested.

A summary of the results of the NCI DTP study as described above for Compound A at 10 µM is set forth in Table 5:

TABLE 5

| Cell Line Panel (# cell lines) | Compound D Mean Growth Percent at 10 µM | $GI_{50}$ | TGI | $LC_{50}$ |
|---|---|---|---|---|
| NSCLC (9) | 62.77 | 3.39E−6 | 7.31E−6 | 2.84E−5 |
| Colon Cancer (6) | 40.49 | 2.36E−6 | 6.45E−6 | 2.28E−5 |
| Breast Cancer (8) | 59.72 | 1.00E−5 | 2.11E−5 | 3.08E−5 |
| Ovarian Cancer (6) | 66.18 | 6.23E−6 | 1.46E−5 | 3.53E−5 |
| Leukemia (6) | 12.31 | 1.09E−6 | 4.28E−6 | 1.34E−5 |
| Renal Cancer (8) | 82.54 | 8.00E−6 | 1.70E−5 | 3.70E−5 |
| Melanoma (8) | 16.46 | 4.09E−6 | 7.74E−6 | 1.59E−5 |
| Prostate (1) | 2.84 | 1.41E−5 | 2.76E−5 | 5.39E−5 |
| CNS (5) | 78.88 | 1.90E−6 | 4.13E−6 | 1.10E−5 |

The results indicate that Compound D at 10 µM concentration had broad-based activity in reducing cell growth against a number of the types of the 60 cell lines. The strongest effects in cell growth reduction were shown against the prostate cancer cell lines, followed by leukemia cell lines, with the least drastic effects shown against renal cancer. $GI_{50}$, TGI and $LC_{50}$ values were all lowest in leukemia and CNS cancer cell lines, indicating the highest potency of Compound D against those cancer cell types.

EXAMPLE 12

Anti-Inflammatory and Anti-Vascular Disease Activity PHK Studies

Anti-inflammatory activity of several of the compounds of the previously described working examples was determined based on the effect of tested compounds on primary human keratinocytes (PHKs) as described above and following the manufacturer's instructions for the various kits used in the studies. While these studies more typically are used mostly for anti-inflammatory investigations, they can also apply to vascular diseases, since the results in keratinocytes may be extrapolated to vascular endothelium.

Only MCP-1 data with PHKs is dose-dependent, so an $IC_{50}$ for MCP-1 can be calculated, but not for the other cytokines Results of the MCP-1 studies on various compounds are shown in the following Table 6.

TABLE 6

| Compound | MCP-1 $IC_{50}$ |
|---|---|
| A | >100 µM |
| C | >100 µM |
| D | 3 µM |
| H | 75 µM |

Results from compounds with anti-inflammatory activity in TNF-α-treated PHK as assayed by MCP-1 protein production are shown in Table 6. $IC_{50}$ concentrations for MCP-1 protein show various degrees of inhibition of this inflammatory cytokine. In results of other of these tests, all compounds that were tested were able to reduce MCP-1 protein production in a dose dependent manner. Compound D showed the strongest inhibition of MCP-1 in TNF-α-treated PHK.

EXAMPLE 13

Permeability Studies as Indicative of Oral Bioavailability

Permeability studies were conducted by an outside contractor on behalf of the assignee of the present invention and application to determine the permeability of Compounds D and G through Caco-2 monolayers. An important factor of oral bioavailability is the ability of a compound to be absorbed in the small intestine. Measurement of drug apparent permeability ($P_{app}$) through cell monolayers is well correlated with human intestinal absorption, and several mammalian cell lines, including Caco-2, LLC-PK1 and MDCK, are appropriate for this measurement (Artursson, P. et al., "Correlation between oral drug absorption in humans and apparent drug permeability coefficients in human intestinal epithelial (Caco-2) cells," *Biochem Biophys Res Comm* 175:880-885 (1991); Stewart, B. H., et al., "Comparison of intestinal permeabilities in multiple in vitro and in situ models: relationship to absorption in humans," *Pharm Res* 12:693 (1995)). P-Glycoprotein (P-gp, encoded by MDR1) is a member of the ABC transporter super family and is expressed in the human intestine, liver and other tissues. Intestinal expression of P-gp may affect the oral bioavailability of drug molecules that are substrates for this transporter. Interaction with P-gp can be studied using direct assays of drug transport in polarized cell systems such as Caco-2 cell monolayers, and human P-gp cDNA-expressing LLC-PKi and MDCK cell monolayers.

Caco-2 cells (human adenocarcinoma colonic cell line Caco-2, ATCC Cat. No. HTB-37, used between passages 18 and 45) were seeded onto BD Falcon™ HTS 24-Multiwell, 1 µm culture inserts (BD Catalog No. 351180) (BD Biosciences Discovery Labware, Woburn, Mass., USA). The cells were cultured for 21-25 days with media replacement every 3-4 days. Monolayer integrity was evaluated by pre-experimental trans-epithelial electrical resistance (TEER) measurements and post-experimental lucifer yellow A to B flux determinations.

Transport buffer was HBSS (Hanks Balanced Salt solution) buffered with the addition of 10 mM HEPES (N-[2-Hydroxyethyl]piperazine-N'-[2-ethanesulfonic acid]), and pH adjusted to 7.4 with NaOH. Receiver solution was prepared by adding 1% DMSO to transport buffer. The test solution was of Compounds D and H in DMSO in transport buffer at a final DMSO concentration of 1%. Donor solutions for two permeability comparator compounds (50 µM [$^3$H]-propranolol as "High" and 50 µM [$^{14}$C]-mannitol as "Low") as well as a positive control P-gp substrate (5 µM [$^3$H]-digoxin) were prepared by diluting aliquots of radiolabeled and non-radiolabeled stock solutions into transport buffer at a final DMSO concentration of 1%.

The test articles Compounds D and H were assayed at a single concentration (1 µM) in both A to B and B to A directions. The donor and receiver solutions were added to the apical or basolateral chambers of the monolayers (depending on the direction of transport to be measured). The monolayers were incubated on an orbital shaker (50 rpm) at 37° C., with ambient humidity and $CO_2$. After 90 minutes, samples from the donor and receiver chambers were removed for analysis.

To determine the extent of non-specific binding of the sample to the assay plate, the sample solution was incubated under the conditions described above in a single well of a 24-well assay plate. After 90 minutes, the sample was removed from each well for analysis. After all samples were collected, lucifer yellow solution was added to each monolayer at a final concentration of 100 µM. The inserts were placed in a new receiver plate containing transport buffer. After a 30 min incubation on an orbital shaker (50 rpm) at 37° C., with ambient humidity and $CO_2$, samples were removed from the receiver chamber to measure percent lucifer yellow flux.

Two permeability comparator compounds representing high permeability (50 µM [$^3$H]-propranolol) and low permeability (50 µM [$^{14}$C]-mannitol) were assayed in the A to B direction, with samples from the donor and receiver chambers taken at one time point of 90 minutes. The control P-gp substrate was 5 µM [$^3$H]-digoxin assayed in both A to B and B to A directions, with samples from the donor and receiver chambers taken at one time point of 90 minutes. Duplicate monolayers were used for each incubation.

Samples were analyzed by LC/MS/MS using peak area ratios to an internal standard. Test article concentrations were calculated based on the peak area ratios obtained for appropriate dilutions of the donor solution containing the test article at the nominal concentration in transport buffer. Samples were diluted as appropriate to ensure that the response was within the linear range of the mass spec detector. Comparator and control samples were analyzed by liquid scintillation counting. Lucifer yellow concentrations were determined using a fluorescence plate reader.

Pre-experimental trans-epithelial electrical resistance (TEER) measurements (mean 411 $\Omega cm^2$) and post-experimental lucifer yellow A to B flux (mean 0.1%) confirmed monolayer integrity. The polarization of the positive control digoxin confirmed a functioning P-gp transport model. The $P_{app}$ values for the permeability comparators mannitol and propranolol were within historical ranges observed at the testing facility with this test system (mean $4.1 \times 10^{-7} \pm SD$ $2.4 \times 10^{-7}$ for mannitol, $1.5 \times 10^{-5} \pm 4.2 \times 10^{-5}$ for propranolol) indicating a properly functioning model.

The results for the permeability comparators mannitol and propranolol as well as for the control P-gp substrate digoxin are reported in the following Table 7.

TABLE 7

| Compound | $P_{app}$ [cm/s] mean | | Polarization Ratio mean | Mass balance mean | |
|---|---|---|---|---|---|
| | A to B | B to A | (B-A/A-B) | A to B | B to A |
| digoxin (5 μM) | 2.28E−06 | 1.24E−05 | 5.4 | 73% | 79% |
| propranolol (50 μM) | 1.42E−05 | n.d. | n.d. | 71% | n.d. |
| mannitol (50 μM) | 5.14E−07 | n.d. | n.d. | 96% | n.d. | n.d.—not determined

Bidirectional permeability data as well as polarization ratios obtained for the test compounds in Caco-2 cell monolayers are reported in Table 8.

TABLE 8

| Test article | Nominal conc. [μM] | $P_{app}$ [cm/s] | | | | Polarization Ratio [B-A/A-B] |
|---|---|---|---|---|---|---|
| | | A to B | | B to A | | |
| Compound D | 1.0 | 1.38E−05 | 1.40E−05 | 2.35E−06 | 2.51E−06 | 0.18 |
| Compound H | 20 | 6.67E−05 | 6.44E−05 | 1.01E−05 | 1.01E−05 | 0.15 |

The recovery of the test articles from the apical and basolateral chambers (mass balance) as well as from a single well of a 24-well culture plate without cells (non-specific binding) at the end of the incubation is reported in Table 9.

TABLE 9

| Test article | Nominal conc. [μM] | Mass Balance * | | | | Non-specific Binding % Recovery |
|---|---|---|---|---|---|---|
| | | A to B | | B to A | | |
| Compound D | 1.0 | 54% | 78% | 48% | 39% | 35% |
| Compound H | 20 | ≥100% | ≥100% | 90% | ≥100% | 96% |

* Mass balance/recovery values of >100% are typically due to increased solubility over the course of the incubation Conclusions The results were very encouraging. Permeability studies in Caco-2 cell monolayer as an in vitro model of intestinal absorption demonstrate that Compound H falls under the high permeability class, and that Compound D falls under the moderate-to-high permeability class as determined by the BCS permeability classification system.

Monolayer TEER results as well as post-experimental lucifer yellow flux results indicated the presence of functional cell monolayers throughout the assay. The positive control for P-gp transport, digoxin, showed polarized transport (polarization ratio of 5.4, Table 7) indicating a properly functioning test system.

Recovery of Compound H from the apical and basolateral chambers at the end of the assay (mass balance) as well as from the assay plate without cells (Table 9) was complete, indicating that the degree of non-specific binding of Compound H to the cells or to the plastic plate did not affect the assay. However, mass balance and non-specific binding determinations showed that Compound D was bound to the plastic plate and/or the cells to a degree that might have reduced the amount of compound available for diffusion and transport. As a result, the apparent $P_{app}$ values and resulting polarization ratios (Table 8) may underestimate the permeability of Compound D and should be used with caution when assigning the compounds to a BCS permeability class as shown in Table 10.

TABLE 10

| Permeability Class[3] | Absorption in Humans[4] | Papp (cm/sec) |
|---|---|---|
| low | <50 % | ≤mannitol |
| moderate | 50-89 % | >mannitol and <propranolol |
| high | ≥90 % | ≥propranolol |

The A-B permeability observed for Compound H (Table 8) in Caco-2 cell monolayers was higher than that of propranolol. Based on the BCS permeability classification (Table 10), Compound H should therefore be considered a high permeability compound. The A-B permeability values observed for Compound D were between those observed for mannitol and propranolol. Based on the BCS permeability classification (Table 10), Compound D would be considered moderate-to-high permeability compounds. As noted above, however, these classifications should be interpreted with caution in light of the degree of binding observed for these compounds.

Compounds D and H showed polarization ratios of 0.1-0.2, indicating that A-B permeability exceeded B-A permeability for these compounds. This finding is inconsistent with P-gp mediated B-A efflux, and may suggest involvement of active A-B flux by a transporter other than P-gp.

The foregoing studies demonstrate that representative compounds of the NDGA derivatives of the present invention would be useful pharmaceutical compounds.

It will be appreciated by those skilled in the art that changes could be made to the embodiments described above without departing from the broad inventive concept thereof.

It is understood, therefore, that this invention is not limited to the particular embodiments disclosed, but it is intended to cover modifications within the spirit and scope of the present invention as defined by the appended claims.

References

1. Trang, T.; Stutak, M.; Quirion, R.; Jhamandas, K. *Br. J. Pharmacol.* 2003, 140, 295-304.
2. Nakadate, T. *Jpn. J. Pharmacol.* 1989, 49, 1-9.
3. Hausott, B.; Greger, H.; Marian, B. *J. Cancer Res. Clin. Oncol.* 2003, 129, 569-576.
4. Fujiwara, T.; Misumi, Y.; Ikehara, Y. *Biochem. Biophys. Res. Commum.* 2003, 301, 927-933.
5. (a) Cheng, J. S.; Jan, C. R. *Toxicol. In Vitro* 2002, 16, 485-490. (b) Wang, J. L.; Chang, H. J.; Tseng, L. L.; Liu, C. P.; Lee, K. C.; Chou, K. J.; Cheng, J. S.; Lo, Y. K.; Su, W.; Law, Y. P.; Chen, W. C.; Chan, R. C.; Jan, C. R. *Pharmacol. Toxicol.* 2001, 89, 301-305. (c) Su, W.; Tseng, L. L.; Lin, M. C.; Chang, H. J.; Lee, K. C.; Chou, K. J.; Lo, Y. K.; Cheng, J. S. Chang, H. T.; Wang, J. L.; Liu, C. P.; Chen, W. C.; Jan, C. R. *Neurochem. Int.* 2002, 40, 249-254. (d) Huang, J. K.; Chen, W. C.; Huang, C. J.; Hsu, S. S.; Chen, J. S.; Cheng, H. H.; Chang, H. T.; Jiann, B. P.; Jan, C. R. *Life Sciences* 2004, 75, 2341-2351.
6. Yamamura, H.; Nagano, N.; Hirano, M.; Muraki, K.; Watanabe, M. Imaizumi, Y. *J. Pharmacol. Exp. Ther.* 1999, 291, 140-146.
7. Ono, K.; Hasegawa, K.; Yoshiike, Y.; Takashima, A.; Yamada, M.; Naiki, H. *J. Neurochem.* 2002, 81, 434-440.
8. Lee, C. H.; Jang, Y. S.; Her, S. J.; Moon, Y. M.; Baek, S. J.; Eling, T. *Exp. Cell. Res.* 2003, 289, 335-341.
9. Hwu, J. R.; Tseng, W. N.; Gnabre, J.; Giza, P.; Huang, R. C. *J. Med. Chem.* 1998, 41, 2994-3000.
10. Huang, R. C.; Li, Y.; Giza, P. E.; Gnabre, J. N.; Abd-Elazem, I. S.; King, K. Y.; Hwu, J. R. *Antiviral Res.* 2003, 58, 57-64.
11. King, K. Y.; Hakimelahi, G. H.; Huang, R. C.; Hwu, J. R. *J. Genetics Mol. Biol.* 2002, 13, 248-257.
12. Gnabre, J. N.; Brady, J. N.; Clanton, D. J.; Ito, Y.; Dittmer, J.; Bates, R. B.; Huang, R. C. *Proc. Natl. Acad. Sci. USA* 1995, 92, 11239-11243.
13. Gnabre, J.; Ito, Y.; Ma, Y.; Huang, R. C. *J. Chromatogr. A* 1996, 719, 353-364
14. Chen, H.; Teng, L.; Li, J.; Park, R.; Mold, D. E.; Gnabre, J.; Hwu, J. R.; Tseng, W. N.; Huang, R. C. *J. Med. Chem.* 1998, 41, 3001-3007.
15. Park, R.; Giza, P. E.; Mold, D. E.; Huang, R. C. *Antiviral Res.* 2003, 58, 35-45.
16. Craigo, J.; Callahan, M.; Huang, R. C.; DeLucia, A. *Antiviral Res.* 2000, 47, 19-28.
17. Chang, C.-C.; Heller, J. D.; Kuo, J.; Huang, R. C. *Proc. Natl. Acad. Sci. USA* 2004, 101, 13239-13244.
18. Heller, J. D.; Kuo, J.; Wu, T. C.; Kast, W. M.; Huang, R. C. *Cancer Res.* 2001, 61, 5499-5504.
19. (a). Park, R.; Chang, C. C.; Liang, Y. C.; Chung, Y.; Henry, R. A.; Lin, E.; Mold, D. E.; Huang, R. C. *Clin. Cancer Res.,* 2005, 11(12), 4601-4609. (b). Chang, C. C.; Liang, Y. C.; Kultz, A.; Hsu, C. I.; Lin, C. F.; Mold, D. E.; Chou, T. C.; Lee, Y. C.; Huang R. C. Published on line Mar. 17, 2006 *Cancer Chemotherapy and Pharmacology.*
20. Nakamura M, Matsuo K., and Nakamura E. *J. Am. Chem. Soc.* 2004, 126, 3686
21. *J. Chem. Soc.* 1934, 1423
22. Nikas S. P. et al. *The AAPS Journal* 2004: 6 (4) Article 30 (http://www.aapsj.org)

We claim:

1. A butane bridge modified nordihydroguaiaretic acid derivative compound (BB-N) having the following general structure (Formula V), and its pharmaceutically acceptable salts:

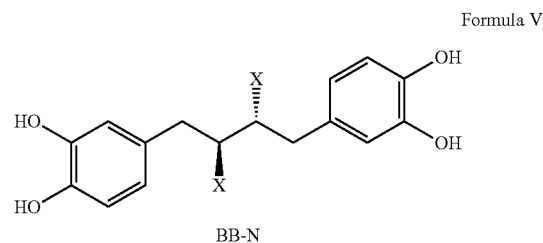

Formula V

BB-N wherein each X is selected from the group consisting of —CN, —CH2Cl, —CH2Br and —CH2F.

2. A composition comprising the BB-N compound of claim 1 and a pharmaceutically acceptable carrier, optionally with other pharmaceutically acceptable excipients.

3. A method of treating a disease selected from breast cancer, lung cancer, skin cancer, esophageal cancer, prostate cancer, glioma or leukemia comprising administering to a subject an amount of the BB-N compound of claim 1 alone or as part of a pharmaceutical composition.

4. A method of treating breast cancer, lung cancer, skin cancer comprising administering to a subject an amount of the BB-N compound of claim 1 alone or as part of a pharmaceutical composition.

5. A method of treating lung cancer comprising administering to a subject an amount of the BB-N compound of claim 1 alone or as part of a pharmaceutical composition.

6. A method of treating skin cancer comprising administering to a subject an amount of the BB-N compound of claim 1 alone or as part of a pharmaceutical composition.

7. A kit comprising a pharmaceutical composition comprising the BB-N compound of claim 1 and instructions for its use in relieving, alleviating or ameliorating breast, lung, skin, esophageal, prostate cancer, glioma or leukemia.

8. The pharmaceutically acceptable salt of claim 1 which is selected from the following acids HCl, HBr, HNO3, MeSO3H, H2SO4, aspartic acid, citric acid, benzenesulfonic acid, camphoric acid, camphorsulfonic acid, ethanesulfonic acid, ethansulfonic acid, formic acid, fumaric acid, galactaric acid, D-gluconic acid, glycolic acid, hippuric acid, L-lactic acid, maleic acid, malic acid, malonic acid, nicotinic acid, palmitic acid, pamoic acid, phosphoric acid, salicylic acid, succinic acid, tartaric acid, p-toluenesulfonic acid.

9. A method of treating-esophageal cancer comprising administering to a subject an amount of the BB-N compound of claim 1 alone or as part of a pharmaceutical composition.

10. A method of treating prostate cancer comprising administering to a subject an amount of the BB-N compound of claim 1 alone or as part of a pharmaceutical composition.

11. A method of treating glioma comprising administering to a subject an amount of the BB-N compound of claim 1 alone or as part of a pharmaceutical composition.

12. A method of treating leukemia comprising administering to a subject an amount of the BB-N compound of claim 1 alone or as part of a pharmaceutical composition.

* * * * *